(12) United States Patent
Thorpe et al.

(10) Patent No.: US 12,066,353 B2
(45) Date of Patent: Aug. 20, 2024

(54) APPARATUSES AND METHODS FOR GAS FLUX MEASUREMENTS

(71) Applicant: Bridger Photonics, Inc., Bozeman, MT (US)

(72) Inventors: Michael James Thorpe, Bozeman, MT (US); Aaron Thomas Kreitinger, Bozeman, MT (US)

(73) Assignee: Bridger Photonics, Inc., Bozeman, MT (US)

( * ) Notice: Subject to any disclaimer, the term of this patent is extended or adjusted under 35 U.S.C. 154(b) by 501 days.

(21) Appl. No.: 16/966,451

(22) PCT Filed: Feb. 1, 2019

(86) PCT No.: PCT/US2019/016267
§ 371 (c)(1),
(2) Date: Jul. 30, 2020

(87) PCT Pub. No.: WO2019/152787
PCT Pub. Date: Aug. 8, 2019

(65) Prior Publication Data
US 2021/0055180 A1    Feb. 25, 2021

Related U.S. Application Data

(60) Provisional application No. 62/662,614, filed on Apr. 25, 2018, provisional application No. 62/625,227, filed on Feb. 1, 2018.

(51) Int. Cl.
*G01M 3/16* (2006.01)
*G01N 33/00* (2006.01)
*G01V 9/00* (2006.01)
*G06F 17/18* (2006.01)

(52) U.S. Cl.
CPC .......... *G01M 3/16* (2013.01); *G01N 33/0004* (2013.01); *G01V 9/007* (2013.01); *G06F 17/18* (2013.01)

(58) Field of Classification Search
CPC ...... G01M 3/16; G01M 3/04; G01N 33/0004; G01V 9/007; G06F 17/18
See application file for complete search history.

(56) References Cited

U.S. PATENT DOCUMENTS 3,925,666 A   12/1975  Allan et al.
3,931,462 A * 1/1976  Exton ...................... G01P 3/36
                                                    356/439
(Continued)

FOREIGN PATENT DOCUMENTS

CA    3142814    *  7/2008  ............... G01N 1/26
CN    205141361 U    4/2016
(Continued)

OTHER PUBLICATIONS

Bara J. Emran et al., "Low-Altitude Aerial Methane Concentration Mapping", Remote Sens. 2017, 9, 823; pp. 1-13.*
(Continued)

*Primary Examiner* — Alexander Satanovsky
(74) *Attorney, Agent, or Firm* — Dorsey & Whitney LLP

(57) ABSTRACT

Embodiments of the disclosure are drawn to apparatus and methods for determining gas flux measurements. A gas plume may be emitted from a source and may be blown by wind in an environment. A measurement system, such as a light detection and ranging (lidar) system may collect a plurality of gas concentration measurements associated with the gas plume at a plurality of locations in the environment. A gas flux may be determined based on one or more of the gas concentration measurements along with a wind speed at a location associated with the gas plume. In some embodiments, a height of the gas plume may be determined, and the wind speed at the height of the gas plume may be determined and used to determine the gas flux.

12 Claims, 16 Drawing Sheets

(56) References Cited

U.S. PATENT DOCUMENTS

| | | |
|---|---|---|
| 4,167,329 A | 9/1979 | Jelalian et al. |
| 4,551,004 A | 11/1985 | Paraskevopoulos |
| 4,593,368 A | 6/1986 | Fridge et al. |
| 4,732,156 A | 3/1988 | Nakamura |
| 4,795,253 A | 1/1989 | Sandridge et al. |
| 4,830,486 A | 5/1989 | Goodwin |
| 5,115,468 A | 5/1992 | Asahi et al. |
| 5,294,075 A | 3/1994 | Vertatschitsch et al. |
| 5,367,399 A | 11/1994 | Kramer |
| 5,371,587 A | 12/1994 | De Groot et al. |
| 5,534,993 A | 7/1996 | Ball et al. |
| 5,548,402 A | 8/1996 | Nogiwa |
| 5,768,001 A | 6/1998 | Kelley et al. |
| 5,859,694 A | 1/1999 | Galtier et al. |
| 6,034,976 A | 3/2000 | Mossberg et al. |
| 6,516,014 B1 | 2/2003 | Sellin et al. |
| 6,822,742 B1 | 11/2004 | Kalayeh et al. |
| 6,864,983 B2 | 3/2005 | Galle et al. |
| 7,215,413 B2 | 5/2007 | Soreide et al. |
| 7,292,347 B2 | 11/2007 | Tobiason et al. |
| 7,511,824 B2 | 3/2009 | Sebastian et al. |
| 7,742,152 B2 | 6/2010 | Hui et al. |
| 7,920,272 B2 | 4/2011 | Sebastian et al. |
| 8,010,300 B1 | 8/2011 | Stearns et al. |
| 8,081,670 B2 | 12/2011 | Belsley |
| 8,121,798 B2 | 2/2012 | Lippert et al. |
| 8,175,126 B2 | 5/2012 | Rakuljic et al. |
| 8,294,899 B2 | 10/2012 | Wong |
| 8,582,085 B2 | 11/2013 | Sebastian et al. |
| 8,730,461 B2 | 5/2014 | Andreussi |
| 8,781,755 B2 | 7/2014 | Wong |
| 8,913,636 B2 | 12/2014 | Roos et al. |
| 9,030,670 B2 | 5/2015 | Warden et al. |
| 9,098,754 B1 | 8/2015 | Stout et al. |
| 9,322,812 B2 * | 4/2016 | Angelescu ............ G01N 30/16 |
| 9,559,486 B2 | 1/2017 | Roos et al. |
| 9,696,423 B2 | 7/2017 | Martin |
| 9,759,597 B2 | 9/2017 | Wong |
| 9,784,560 B2 | 10/2017 | Thorpe et al. |
| 9,864,060 B2 | 1/2018 | Sebastian et al. |
| 9,970,756 B2 | 5/2018 | Kreitinger et al. |
| 10,247,538 B2 | 4/2019 | Roos et al. |
| 10,928,182 B2 | 2/2021 | Roos et al. |
| 11,105,621 B2 | 8/2021 | Kreitinger et al. |
| 11,112,308 B2 | 9/2021 | Kreitinger et al. |
| 11,391,567 B2 | 7/2022 | Thorpe et al. |
| 11,422,244 B2 | 8/2022 | Thorpe et al. |
| 11,422,258 B2 | 8/2022 | Thorpe et al. |
| 2002/0071122 A1 | 6/2002 | Kulp et al. |
| 2003/0043437 A1 | 3/2003 | Stough et al. |
| 2004/0088113 A1 | 5/2004 | Spoonhower et al. |
| 2004/0105087 A1 | 6/2004 | Gogolla et al. |
| 2005/0078296 A1 | 4/2005 | Bonnet |
| 2005/0094149 A1 | 5/2005 | Cannon |
| 2006/0050270 A1 | 3/2006 | Elman |
| 2006/0162428 A1 | 7/2006 | Hu et al. |
| 2006/0203224 A1 | 9/2006 | Sebastian et al. |
| 2008/0018881 A1 | 1/2008 | Hui et al. |
| 2008/0018901 A1 | 1/2008 | Groot |
| 2009/0046295 A1 | 2/2009 | Kemp et al. |
| 2009/0110004 A1 | 4/2009 | Chou et al. |
| 2009/0153872 A1 | 6/2009 | Sebastian et al. |
| 2009/0257622 A1 | 10/2009 | Wolowelsky et al. |
| 2010/0007547 A1 | 1/2010 | D'Addio |
| 2010/0091278 A1 | 4/2010 | Liu et al. |
| 2010/0131207 A1 * | 5/2010 | Lippert .................. G01S 17/95 |
| | | 702/49 |
| 2010/0141261 A1 | 6/2010 | Overby et al. |
| 2011/0069309 A1 | 3/2011 | Newbury et al. |
| 2011/0164783 A1 | 7/2011 | Hays et al. |
| 2011/0188029 A1 | 8/2011 | Schmitt et al. |
| 2011/0205523 A1 | 8/2011 | Rezk et al. |
| 2011/0213554 A1 * | 9/2011 | Archibald ............. G01V 9/007 |
| | | 702/6 |
| 2011/0273699 A1 | 11/2011 | Sebastian et al. |
| 2011/0292403 A1 | 12/2011 | Jensen et al. |
| 2012/0038930 A1 | 2/2012 | Sesko et al. |
| 2012/0106579 A1 | 5/2012 | Roos et al. |
| 2012/0274938 A1 | 11/2012 | Ray |
| 2012/0293358 A1 | 11/2012 | Itoh |
| 2013/0104661 A1 | 5/2013 | Klotz et al. |
| 2013/0162976 A1 | 6/2013 | Dakin et al. |
| 2014/0002639 A1 | 1/2014 | Cheben et al. |
| 2014/0036252 A1 | 2/2014 | Amzajerdian et al. |
| 2014/0139818 A1 | 5/2014 | Sebastian et al. |
| 2014/0204363 A1 | 7/2014 | Slotwinski et al. |
| 2015/0019160 A1 | 1/2015 | Thurner et al. |
| 2015/0059444 A1 * | 3/2015 | Rella .................. G01N 33/0011 |
| | | 73/30.01 |
| 2015/0185313 A1 | 7/2015 | Zhu |
| 2015/0355327 A1 | 12/2015 | Goodwin et al. |
| 2016/0033643 A1 | 2/2016 | Zweigle et al. |
| 2016/0123718 A1 | 5/2016 | Roos et al. |
| 2016/0123720 A1 | 5/2016 | Thorpe et al. |
| 2016/0131514 A1 | 5/2016 | Babin et al. |
| 2016/0202225 A1 | 7/2016 | Feng et al. |
| 2016/0259038 A1 | 9/2016 | Retterath et al. |
| 2016/0261091 A1 | 9/2016 | Santis et al. |
| 2016/0329681 A1 | 11/2016 | Tulip |
| 2017/0089829 A1 | 3/2017 | Bartholomew |
| 2017/0097274 A1 | 4/2017 | Thorpe et al. |
| 2017/0097302 A1 | 4/2017 | Kreitinger et al. |
| 2017/0115218 A1 | 4/2017 | Huang et al. |
| 2017/0131394 A1 | 5/2017 | Roger et al. |
| 2017/0146335 A1 | 5/2017 | Martinez et al. |
| 2017/0168161 A1 | 6/2017 | Shapira et al. |
| 2017/0171397 A1 | 6/2017 | Mitsumori et al. |
| 2017/0191898 A1 | 7/2017 | Rella et al. |
| 2017/0343333 A1 | 11/2017 | Thorpe et al. |
| 2018/0188369 A1 | 7/2018 | Sebastian et al. |
| 2018/0216932 A1 | 8/2018 | Kreitinger et al. |
| 2018/0224548 A1 | 8/2018 | Hariyama et al. |
| 2019/0013862 A1 | 1/2019 | He et al. |
| 2019/0086517 A1 | 3/2019 | Puglia et al. |
| 2019/0170500 A1 | 6/2019 | Roos et al. |
| 2019/0285409 A1 | 9/2019 | Kreitinger et al. |
| 2019/0383596 A1 | 12/2019 | Thorpe et al. |
| 2020/0011994 A1 | 1/2020 | Thorpe et al. |
| 2020/0149883 A1 | 5/2020 | Thorpe et al. |
| 2020/0182978 A1 | 6/2020 | Maleki et al. |
| 2020/0241139 A1 | 7/2020 | Roos et al. |
| 2020/0278432 A1 | 9/2020 | Thorpe et al. |
| 2020/0355552 A1 | 11/2020 | Kreitinger et al. |
| 2021/0190953 A1 | 6/2021 | Roos et al. |
| 2021/0293960 A1 | 9/2021 | Kreitinger et al. |
| 2023/0228876 A1 | 7/2023 | Roos et al. |
| 2023/0243648 A1 | 8/2023 | Kreitinger et al. |
| 2023/0314266 A1 | 10/2023 | Kreitinger et al. |

FOREIGN PATENT DOCUMENTS

| | | | |
|---|---|---|---|
| FR | 2691809 A1 | 12/1993 | |
| JP | H07333097 | * 12/1995 | ............ G01M 3/04 |
| JP | 2005172442 | * 6/2005 | ............ G01W 1/00 |
| WO | 2010127151 A2 | 11/2010 | |
| WO | 2014088650 A1 | 6/2014 | |
| WO | 2016064897 A1 | 4/2016 | |
| WO | 2017187510 A1 | 11/2017 | |
| WO | 2018067158 A1 | 4/2018 | |
| WO | 2018170478 A1 | 9/2018 | |
| WO | 2019060901 A1 | 3/2019 | |
| WO | 2019070751 A1 | 4/2019 | |
| WO | 2019079448 A1 | 4/2019 | |
| WO | 2019099567 A1 | 5/2019 | |

OTHER PUBLICATIONS

J. D. Wilson et al., "Ground-to-Air Gas Emission Rate Inferred from Measured Concentration Rise within a Disturbed Atmospheric Surface Layer", Journal of Applied Meteorology and Climatology, vol. 49, pp. 1818-1830, Sep. 2010.*

Thomas Keefer, "The Relation of Turbulence to Diffusion in Open-Channel Flows", United States Geological Survey, 2017, 141 pages, https://pubs.usgs.gov/of/1972/0206/report.pdf.*

U.S. Appl. No. 17/399,106 titled "High-Sensitivity Gas-Mapping 3D Imager and Method of Operation" filed Aug. 12, 2021.

U.S. Appl. No. 17/408,886 titled "Apparatuses and Methods for Anomalous Gas Concentration Detection" filed Aug. 23, 2021.

U.S. Appl. No. 17/858,870 titled "Gas-Mapping 3D Imager Measurement Techniques and Method of Data Processing" filed Jul. 6, 2022.

Cao , et al., "Etalon Eifects Analysis in Tunable Diode Laser Absorption Spectroscopy Gas Concentration Detection System Based on Wavelength Modulation Spectroscopy", 2010 Symposium on Photonics and Optoelectronics, 2010, pp. 1-5.

International Search Report and Written Opinion dated Aug. 1, 2018 for PCT Application No. PCT/US2018/023004, 18 pgs.

International Search Report and Written Opinion dated Jan. 29, 2019 for PCT Application No. PCT/US2018/052682, 16 pgs.

International Search Report and Written Opinion dated Mar. 15, 2019 for PCT Application No. PCT/US2018/061120; 17 pgs.

International Search Report and Written Opinion dated Nov. 30, 2018 for PCT Application No. PCT/US2018/054016, 18 pages.

International Search Report and Written Opinion for Application No. PCT/US2019/042422, dated Oct. 24, 2019.

International Search Report dated Feb. 16, 2016 for International Application No. PCT/US2015/057814.

International Search Report dated Jan. 19, 2016 for International Application No. PCT/US2015/058051.

International Search Report dated Jun. 7, 2019 for International Application No. PCT/US2019/016267.

U.S. Appl. No. 16/650,816 titled "Digitization Systems and Techniques and Examples of Use in FMCW Lidar Methods and Apparatuses" filed Mar. 25, 2020.

U.S. Appl. No. 16/734,769 titled "Gas-Mapping 3D Imager Measurement Techniques and Method of Data Processing" filed Jan. 6, 2020.

U.S. Appl. No. 16/753,314 titled "Processing Temporal Segments of Laser Chirps and Examples of Use in FMCW Lidar Methods and Apparatuses" filed Apr. 2, 2020.

U.S. Appl. No. 16/756,408 titled "Apparatuses and Methods for a Rotating Optical Reflector" filed Apr. 15, 2020.

U.S. Appl. No. 16/763,955 titled "Apparatuses and Methods for Anomalous Gas Concentration Detection" filed May 13, 2020.

Written Opinion of the International Searching Authority: PCT application No. PCT/US2018/023004 dated Aug. 1, 2018.

International Search Report and Written Opinion for PCT Application No. PCT/US2018/056285 dated Dec. 20, 2018.

International Search Report and Written Opinion received for PCT/US2015/057814 dated Feb. 16, 2016.

International Search Report and Written Opinion received for PCT/US2015/058051 dated Jan. 19, 2016.

Amann, et al., ""Laser ranging: a critical review of usual techniques for distance measurement," Optical Engineering, vol. 40(1) pp. 10-19 (Jan. 2001)".

Barber, et al., ""Accuracy of Active Chirp Linearization for Broadband Frequency Modulated Continuous Wave Ladar," Applied Optics, vol. 49, No. 2, pp. 213-219 (Jan. 2010)".

Barker, , ""Performance enhancement of intensity-modulated laser rangefinders on natural surfaces"", SPIE vol. 5606, pp. 161-168 (Dec. 2004).

Baumann, et al., ""Speckle Phase Noise in Coherent Laser Ranging: Fundamental Precision Limitations," Optical Letters, vol. 39, Issue 16, pp. 4776-4779 (Aug. 2014)".

Boashash, , ""Estimating and Interpreting the Instantaneous Frequency of a Signal-Part 2: Algorithms and Applications"", Proceedings of the IEEE, vol. 80, No. 4, pp. 540-568 (Apr. 1992).

Bomse, et al., ""Frequency modulation and wavelength modulation spectroscopies: comparison of experimental methods using a lead-salt diode laser"", Appl. Opt., 31, pp. 718-731 (Feb. 1992).

Choma, et al., ""Sensitivity Advantage of Swept Source and Fourier Domain Optical Coherence Tomography," Optical Express, vol. 11, No. 18, 2183 (Sep. 2003)".

Ciurylo, , ""Shapes of pressure- and Doppler-broadened spectral lines in the core and near wings"", Physical Review A, vol. 58 No. 2, pp. 1029-1039 (Aug. 1998).

Dharamsi, , "A theory of modulation spectroscopy with applications of higher harmonic detection", J. Phys. D: Appl. Phys 29, pp. 540-549 (Jun. 1995;1996) (Retrieved Jan. 16, 2017).

Emran, Bara J. et al., "Low-Altitude Aerial Methane Concentration Mapping", School of Engineering, The University of British Columbia, Aug. 10, 2017, pp. 1-12.

Fehr, et al., ""Compact Covariance Descriptors in 3D Point Clouds for Object Recognition"", 2012 IEEE International Conference on Robotics and Automation, pp. 1793-1798, (May 2012).

Fransson, Karin et al., "Measurements of VOCs at Refineries Using the Solar Occultation Flux Technique", Department of Radio and Space Science, Chalmers University of Technology, 2002, 1-19.

Fujima, et al., ""High-resolution distance meter using optical intensity modulation at 28 GHz"", Meas. Sci. Technol. 9, pp. 1049-1052 (May 1998).

Gilbert, et al., ""Hydrogen Cyanide H13C14N Absorption Reference for 1530 nm to 1565 nm Wavelength Calibration—SRM 2519a"", NIST Special Publication 260-137 2005 ED, 29 pages, (Aug. 2005).

Iiyama, et al., "Linearizing Optical Frequency—Sweep of a Laser Diode for FMCW Reflectrometry", Iiyama et al. Journal of Lightwave Technology, vol. 14, No. 2, Feb. 1996.

Iseki, et al., "A Compact Remote Methane Sensor using a Tunable Diode Laser", Meas. Sci. Technol., 11, 594, pp. 217-220 (Jun. 2000).

Jia-Nian, et al., ""Etalon effects analysis in tunable diode laser absorption spectroscopy gas concentration detection system based on wavelength modulation spectroscopy"", IEEE SOPO, pp. 1-5 (Jul. 2010).

Johnson, et al., ""Using Spin-Images for Efficient Object Recognition in Cluttered 3D Scenes"", IEEE Transactions on Pattern Analysis and Machine Intelligence, vol. 21, No. 5, 37 pages (Published May 1999).

Karlsson, et al., "Linearization of the frequencysweep of a frequency—modulated continuous-wave semiconductor laser radar and the resulting ranging performance", Christer J. Karlsson et al., Applied Optics, vol. 38, No. 15, May 20, 1999, pp. 3376-3386.

Karmacharya, et al., ""Knowledge guided object detection and indentification in 3D point clouds"", SPIE 9528, 952804-952804-13 (Jun. 2015).

Lenz, Dawn et al., "Flight Testing of an Advanced Airborne Natural Gas Leak Detection System", ITT Industries Space Systems Division, Oct. 2005.

Lu, et al., "Differential wavelength-scanning heterodyne interferometer for measuring large step height", Applied Optics, vol. 41, No. 28, Oct. 1, 2002.

Masiyano, et al., ""Use of diffuse reflections in tunable diode laser absorption spectroscopy: implications of laser speckle for gas absorption measurements"", Appl. Phys. B 90, pp. 279-288 (Feb. 2008).

Mather, T.A. et al., "A reassessment of current volcanic emissions from the Central American arc with specific examples from Nicaragua", Journal of Volcanology and Geothermal Research, Nov. 2004, 297-311.

Ngo, et al., ""An isolated line-shape model to go beyond the Voigt profile in spectroscopic databases and radiative transfer codes"", Journal of Quantitative Spectroscopy and Radiative Transfer, 129, pp. 89-100 (Nov. 2013).

Olsovsky, et al., ""Chromatic Confocal Microscopy for Multi-depth Imaging of Epithelial Tissue," Biomedical Optics Express, vol. 4, No. 5, pp. 732-740 (May 2013)".

Paffenholz, , ""Direct geo-referencing of 3D point clouds with 3D positioning sensors"", (Doctoral Thesis), Leibniz Universität Hannover, 138 pages (Sep. 2012).

Polyanksy, et al., ""High-Accuracy CO2 Line Intensities Determined from Theory and Experiment"", Physical Review Letters, 114, 5 pages (Jun. 2015).

Rao, , ""Information and the accuracy attainable in the estimatin of statistical parameters"", Bull. Calcutta Math. Soc., 37,pp. 81-89 (1945, reprinted 1992) (Retrieved Jan. 10, 2017).

Riris, et al., ""Airborne measurements of atmospheric methane column abundance using a pulsed integrated-path differential absorption lidar"", Applied Optics, vol. 51, No. 34, pp. 8296-8305 (Dec. 2012).

Roos, et al., ""Ultrabroadband optical chirp linearization for precision metrology application"", Optics Letters, vol. 34 No.23, pp. 3692-3694 (Dec. 2009).

Roos, et al., "Ultrabroadband optical chirp linearization for precision metrology applications", Optics Letters, vol. 34, Issue 23, pp. 3692-3694 (2009).

Rothman, et al., ""The HITRAN 2008 molecular spectroscopic database"", Journal of Quantitative Spectroscopy & Radiative Transfer, 110, pp. 533-572 (Jul. 2009).

Rusu, et al., ""Fast Point Feature Histograms (FPFH) for 3D Registration"", IEEE Int. Conf. Robot., pp. 3212-3217 (May 2009).

Sandsten, et al., ""Volume flow calculations on gas leaks imaged with infrared gas-correlation"", Optics Express, vol. 20, No. 18, pp. 20318-20329 (Aug. 2012).

Sheen, et al., "Frequency Modulation Spectroscopy Modeling for Remote Chemical Detection." PNNL 13324 (Sep. 2000).

Sheen, , ""Frequency Modulation Spectroscopy Modeling for Remote Chemical Detection"", PNNL 13324, 51 pages (Sep. 2000).

Silver, , ""Frequency-modulation spectroscopy for trace species detection: theory and comparison among experimental methods"", Appl. Opt., vol. 31 No.6, pp. 707-717 (Feb. 1992).

Sirat, et al., ""Conoscopic Holography," Optics Letters, vol. 10, No. 1 (Jan. 1985)".

Sivananthan, , Integrated Linewidth Reduction of Rapidly Tunable Semiconductor Lasers Sivananthan, Abirami, Ph.D., University of California, Santa Barbara, 2013, 206; 3602218.

Stone, et al., ""Performance Analysis of Next-Generation LADAR for Manufacturing, Construction, and Mobility," NISTIR 7117 (May 2004)".

Thoma, Eben D. et al., "Open-Path Tunable Diode Laser Absorption Spectroscopy for Acquisition of Fugitive Emission Flux Data", Journal of the Air & Waste Management Association (vol. 55), Mar. 1, 2012, 658-668.

Twynstra, et al., ""Laser-absorption tomography beam arrangement optimization using resolution matrices"", Applied Optics, vol. 51, No. 29, pp. 7059-7068 (Oct. 2012).

Xi, et al., "Generic real-time uniorm K-space sampling method for high-speed swept-Source optical cohernece tomography", Optics Express, vol. 18, No. 9, pp. 9511-9517 (Apr. 2010).

Zakrevskyy, et al., ""Quantitative calibration- and reference-free wavelength modulation spectroscopy"", Infrared Physics & Technology, 55, pp. 183-190 (Mar. 2012).

Zhao, et al., ""Calibration-free wavelength-modulation spectroscopy based on a swiftly determined wavelength-modulation frequency response function of a DFB laser"", Opt. Exp., vol. 24 No. 2, pp. 1723-1733 (Jan. 2016).

Zhag, Yanzeng et al., "Lidar Measurement of Ammonia Cancentratims and Fluxes in a Plume from a Point Source", Cooperative Institute for Research in Environmental Studies, University of Colorado/NOAA (vol. 19), Jan. 2002, 1928-1938.

U.S. Appl. No. 17/259,921 titled "Methods and Apparatuses for Range Peak Pairing and High-Accuracy Target Tracking Using FMCW Ladar Measurements" filed Jan. 12, 2021.

* cited by examiner

APPARATUSES AND METHODS FOR GAS FLUX MEASUREMENTS

This application is a 35 U.S.C. § 371 National Stage Application of PCT Application No. PCT/US2019/016267, filed Feb. 1, 2019, which claims the benefit of U.S. Provisional Application No. 62/625,227, filed Feb. 1, 2018, and U.S. Provisional Application No. 62/662,614, filed Apr. 25, 2018, the entire contents of which are hereby incorporated by references, in their entirely, for any purpose.

STATEMENT REGARDING RESEARCH & DEVELOPMENT

This invention was made with government support under DE-AR0000544 awarded by the Department of Energy. The government has certain rights in the invention.

BACKGROUND

Sensors for measuring and monitoring gas concentrations over large areas are important tools for wide variety of traditional and emerging applications. Many sensor technologies have been deployed for large-area gas concentration measurements and monitoring. Examples include active remote sensing techniques, such as certain forms of light detection and ranging (lidar) and open-path spectroscopy systems, as well as passive remote sensing techniques including imaging spectrometers and optical gas cameras. In addition to remote sensing techniques, distributed point sensor networks and mobile point sensors have been deployed, which may require gas intake for measurements.

Several performance tradeoffs exist between the various types of remote sensors. For instance, passive remote sensors may enable high measurement rates, and therefore may be used to more rapidly cover large areas. However, passive sensors may exhibit low detection reliability, higher false positive rates, and poorer sensitivity compared to their active remote sensor counterparts. For example, state-of-the-art airborne optical gas cameras typically quote methane detection sensitivities in the thousands of ppm-m, and are highly dependent on ambient conditions. Shadows, clouds, nighttime, and varying background reflectivity from one object or portion of a scene to the next can confound passive remote sensors and make reliable, sensitive detection challenging. Passive sensors may therefore be best suited for detection of only the very largest leaks and may be operated from space satellite platforms to cover large areas. The relatively poor sensitivity of passive measurements may also result in a relatively high probability of missed detections— in some cases of relatively large leaks. In contrast, lidar techniques such as wavelength modulation spectroscopy (WMS), differential absorption lidar (DIAL) and tunable diode laser absorption spectroscopy (TDLAS) may achieve methane detection concentration sensitivities of tens of ppm-m or less, which may enable much more comprehensive leak detection, including during windy, cloudy, or varying background conditions.

In addition to detection sensitivity, lidar sensors may benefit from high spectral selectivity of targeted gas species compared to passive sensors. These properties of lidar measurements may result from the relative consistency of active laser illumination of remote targets and selective detection schemes used to process light signals received by lidar sensors. Selectivity of the target gas species may make lidar sensors especially well-suited for quantification of regions of anomalous gas concentration. Specifically, leak rate quantification of detected plumes may be desirable because it may allow classification and prioritization of detected leaks. There is an existing unsolved need to achieve increased accuracy for quantifying gas leak rates or fluxes.

SUMMARY

In at least one aspect, the present disclosure may relate to a method which may include collecting a gas plume image. The gas plume image may include a plurality of gas concentration measurements. The method may include determining a region of unperturbed flow and determining a wind velocity associated with the region of unperturbed flow. The method may include determining a gas flux based on at least one of the gas concentration measurements located in the region of unperturbed flow and the wind velocity.

The method may also include determining a vertical statistical moment or vertical distribution of the gas plume associated with the region of unperturbed flow. The method may also include determining a vertical wind speed profile associated with the region of unperturbed flow and determining the gas flux based on the vertical statistical moment or vertical distribution and the vertical wind speed profile.

Determining the region of unperturbed flow may be based on a topographic map of an environment associated with the gas plume. The method may also include determining a plurality of range measurements while collecting the gas plume image and generating the topographic map based on the plurality of range measurements. Determining the region of unperturbed flow may be based on a distribution of the plurality of gas concentration measurements along a plume heading.

The method may also include based on the determined gas flux, evacuating an area, measuring an environmental hazard, locating a gas leak, determining a possible repair, conducting a repair, ensuring regulatory compliance, or combinations thereof.

In at least one aspect, the present disclosure may relate to a method. The method may include collecting, from a mobile platform, a plurality of measurements of a gas plume. The method may include determining a vertical statistical moment or vertical distribution of gas concentration based on the plurality of measurements of the gas plume. The method may include determining a vertical wind speed profile corresponding to the vertical statistical moment or vertical distribution. The method may include determining a gas flux based on the vertical statistical moment or the vertical distribution of the gas concentration and the wind speed profile.

The plurality of measurements may be taken from at least two angles with respect to the gas plume. The vertical statistical moment or the vertical distribution of the gas concentration may be determined based on the at least two angles. Determining the vertical statistical moment may include triangulating the vertical statistical moment based on a first measurement taken from a first angle, and a second measurement taken from a second angle. Determining the vertical distribution profile may include determining a plurality of gas concentrations associated with a plurality of grid cells and determining a plurality of vertical distribution profiles along a plurality of vertical columns of the plurality of grid cells. Determining the vertical statistical moment or the vertical distribution of the gas concentration may be based on topographic information.

The method may also include collecting range measurements from the mobile platform and generating the topographic information based on the range measurements. The method may also include determining a region of unperturbed wind flow and determining the vertical statistical moment or the vertical distribution of the gas concentration and the vertical wind speed profile in the region of unperturbed wind flow.

In at least one aspect, the present disclosure may relate to a method. The method may include collecting a plurality of measurements of a gas plume and determining a plurality of vertical gas concentration profiles based on the plurality of measurements of the gas plume. The method may include determining a vertical wind speed profile associated with one or more of the plurality of vertical gas concentration profiles. The method may include determining a flux of the gas plume based on the vertical wind speed profile and the plurality of vertical gas concentration profiles.

The vertical wind speed profile may be based, at least in part, on weather model data. The vertical wind speed profile may be based on fitting at least one wind speed measurement to a wind model. The plurality of measurements may be taken from a plurality of angles with respect to the gas plume and the plurality of vertical gas concentration profiles may be based, at least in part, on the plurality of angles.

The method may also include determining a region of unperturbed wind flow and determining the vertical statistical moment or vertical distribution and the vertical wind speed profile in the region of unperturbed wind flow.

In at least one aspect, the present disclosure may relate to a system, which may include an optical system, at least one processor, and at least one memory. The optical system may collect a plurality of gas concentration measurements in an environment from a plurality of angles. The at least one memory may be encoded with executable instructions. The executable instructions, when executed by the at least one processor, may cause the system to determine a plurality of vertical gas concentration profiles based on the plurality of gas concentration measurements and the plurality of angles. The executable instructions, when executed by the at least one processor, may cause the system to determine a gas flux based on the plurality of vertical gas concentration profiles and a vertical wind speed distribution associated with at least one of the plurality of vertical gas concentration profiles.

The optical system may also collect topographic information about the environment. The executable instructions, when executed by the at least one processor, may also cause the system to determine the vertical wind speed distribution based, at least in part, on the topographic information.

The executable instructions, when executed by the at least one processor, may also cause the system to determine a region of unperturbed wind flow in the environment. The executable instructions, when executed by the at least one processor, may also cause the system to filter out gas concentrations measurements outside the region of unperturbed wind flow and determine the gas flux based on the filtered gas concentration measurements and the vertical wind speed profile in the region of unperturbed wind flow.

The system may also include a mobile platform which may move the optical system relative to the environment. The optical system may be positioned on the mobile platform, and the at least one processor and the at least one memory may be remote from the mobile platform. The executable instructions, when executed by the at least one processor, may also cause the system to determine the vertical wind speed distribution based on a weather model.

DETAILED DESCRIPTION

Figure 1:
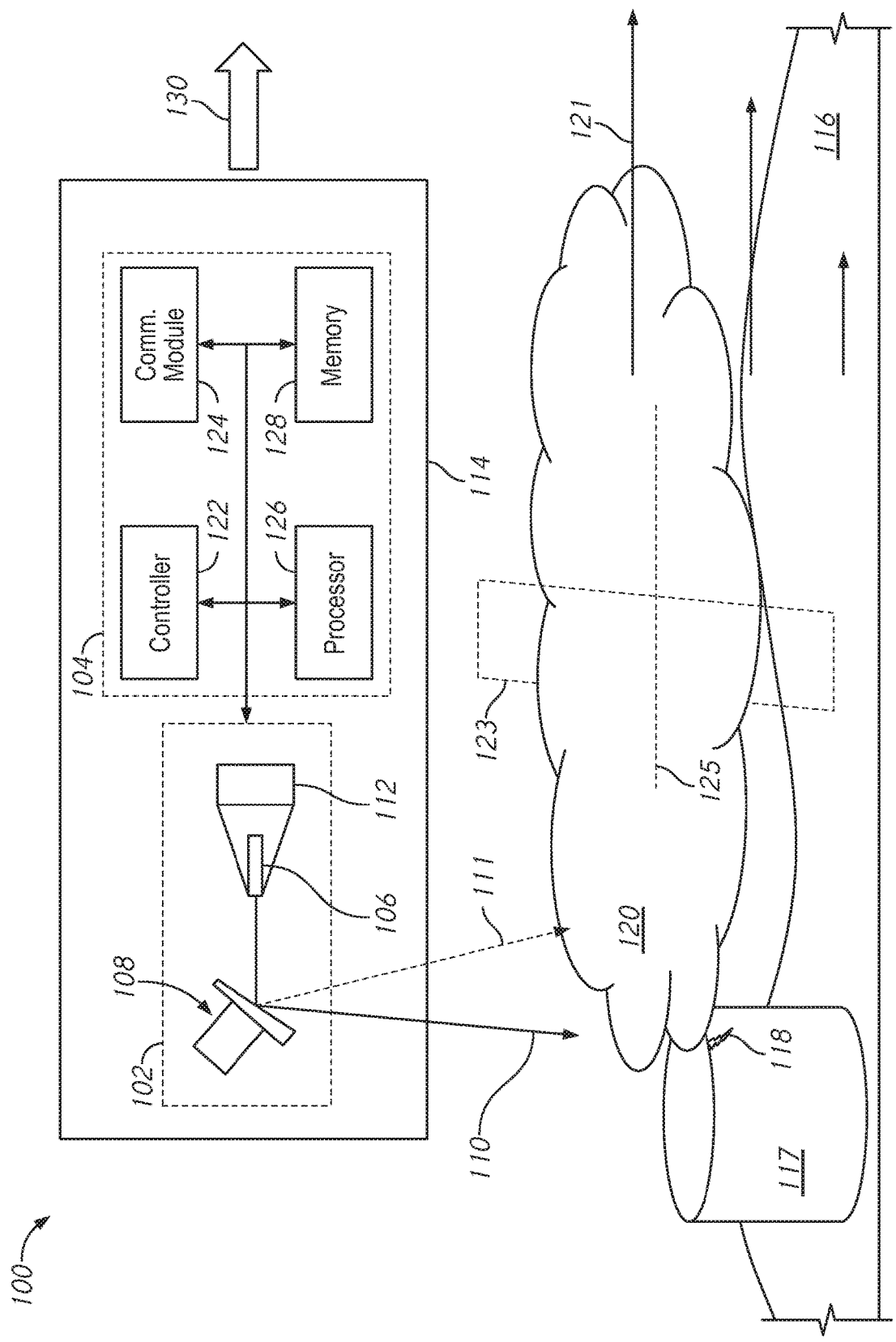
FIG. 1 is a block diagram of a measurement system according to an embodiment of the present disclosure.

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims.

There are many applications where it may be desirable to determine a flux of a gas in an environment. The flux represents the rate of flow of the gas in time and may refer to the rate of flow from a leak or through a given area. In some embodiments, an amount of gas may not normally be present in the environment, and it may be emitted from a particular source. Measurements of the gas flux may be complicated by the fact that as the gas is emitted, it is moved by the wind in the environment. This may cause the gas to take the form of a plume, which may generally extend along a direction downwind from the source. Information about gas concentrations in the plume may be combined with wind velocity information to obtain flux information. However, available wind estimates may not be accurate for the locations within the gas plume, resulting in inaccurate flux determination. For example, wind velocity may have a strong dependence on height, and available wind measurements may not be taken at the same height as the gas concentration measurements. For remote gas concentration measurements of a plume, the height or vertical distribution of the plume is often not known, or challenging to obtain, which may introduce significant uncertainty or error into the flux calculation due to uncertainty of the wind speed at the unknown plume height. In another example, the topography of the environment may complicate both wind velocity and gas movement in certain regions of the environment. It may be desirable to increase the accuracy of gas flux measurements by obtaining more accurate information about the wind velocity at locations matching the gas plume.

The present disclosure provides examples of apparatuses and methods for gas flux measurements with improved accuracy. A gas plume image may be generated by collecting gas concentration measurements at a variety of different locations in an environment. A flux of the gas plume may be determined based on the gas concentration measurements and a wind speed associated with at least one location in the gas plume. However, such a flux determination may be confounded or inaccurate due to perturbed flow of the gas. In some embodiments, the wind speed and flux determination may be associated with an unperturbed flow region of the gas plume in which there is (relatively) unobstructed wind flow. Such a flux determination may be more accurate than a similar flux determination in a region of perturbed wind flow. In some embodiments, the unperturbed flow region may be identified based on the gas concentration measurements and/or topographic data about the environment. In some embodiments, the wind speed at the height of the gas plume may be determined. The height of the gas plume may be determined and the wind speed at that height may be determined (which may be based on adjusting the wind speed measured at a different height). Information about the gas concentration at a location within the unperturbed flow region may be combined with wind speed information at that location in order to determine the flux. In some embodiments, tomographic sectioning may be used to build a 3D data set of gas concentration information, which may be combined with wind speed information at locations within the 3D data set to determine the flux.

FIG. 1 is a block diagram of a measurement system according to an embodiment of the present disclosure. The measurement system 100 includes an optical system 102 and a computing system 104. The optical system 102 includes a transmitter 106, which provides emitted light to a scanner 108, which directs an example light ray 110 towards an environment 116. The optical system 102 may direct measurements along a plurality of angles, as represented by light ray 110 and light ray 111 with respect to the environment. The environment 116 may include a gas source 118 which emits a gas plume 120 which may be blown across the environment 116 by the wind 121. In the example of FIG. 1, the gas source 118 is shown as a leak, located on a structure 117 in the environment 116. The light ray 110 may interact with the gas plume 120, and a portion of the light may return to the optical system 102 and be measured by a receiver 112. The computing system 104 includes one or more components such as a controller 122, a communications module 124, a processor 126, and/or a memory 128. All or part of the measurement system 100 may be mounted on a mobile platform 114, which may have a direction of motion 130 relative to the environment 116. The measurement system 100 may determine a gas concentration at one or more heights 125 and may determine a flux based on the gas concentration and an associated wind speed 121.

In some embodiments, the measurement system 100 may include a light detection and ranging (lidar) system. The lidar system may use laser light to detect gas concentration of a gas plume 120, and/or optionally performing one or more other measurements (e.g., range or distance to a surface of the environment 116). In some embodiments, the measurement system 100 may include a spectroscopic system (e.g., wavelength modulation spectroscopy) and one or more properties of the gas plume 120 (e.g., type, composition, concentration, etc.) may be determined based, at least in part, on spectroscopic measurements. In some embodiments, the measurement system 100 may use wavelength modulation spectroscopy (WMS), where a laser used to illuminate the environment 116 is modulated.

The measurement system 100 may perform a plurality of spectroscopic measurements, which may be distributed across the environment 116. In some embodiments, the measurement system 100 may be fixed relative to the environment 116. In some embodiments, the measurement system 100 may be mounted on a mobile platform 114, which may move along a direction of motion 130 relative to the environment 116. In some embodiments, the measurement system 100 may scan the beam (e.g., light ray 110) (and/or the field of view of the receiver 112) across the environment 116. The scanning of the measurements over time (and/or the motion of the mobile platform 114) may allow the measurement system 100 to collect data from a plurality of different locations, and from a plurality of different angles, in the environment 116. Although the example of FIG. 1 may generally show the direction of motion 130 as aligned with a direction of the wind 121, the direction of motion 130 may have any relationship with the direction of the wind 121. For example, in some embodiments it may be beneficial for the mobile platform 114 to move generally perpendicular to a direction of the wind 121.

The measurement system 100 may take the plurality of spectroscopic measurements from a plurality of different angles, which are schematically represented by light ray 110 and light ray 111. A given location in the environment 116, which may include a location of a plume above the ground, may be scanned by measurement system 100 from multiple angles (e.g., a first measurement from a first angle and a second measurement from a second angle). The measurement system 100 may record (e.g., in memory 128) information about the angle at which a given measurement is taken. While only two light rays are shown in the example of FIG. 1, any number of different angles may be used in other example embodiments. In some embodiments, the measurement system 100 may take measurements along a single beam path, which may be scanned across the environment 116 (e.g., by scanner 108) to generate measurements from the plurality of angles. In some embodiments, the measurement system 100 may be capable of taking measurements from multiple angles simultaneously or in short succession. In some embodiments, the measurement system may take measurements from multiple angles simultaneously or in short succession, and may also scan the environment 116.

The information gathered by the measurement system 100 may be used to determine one or more properties of the gas plume 120 such as a concentration of the gas plume 120. Each measured concentration of the gas plume 120 may be associated with a measurement light path (e.g., along light ray 110 and/or 111). The measurement light paths may differ in angle or displacement to each other due to motion of the mobile platform 114 and/or scanning of the receiver's 112 field of view (e.g., by scanner 108). In some embodiments, a given location within the environment, which given location may be a location within a plume above ground, may be intersected by two or more measurement light paths, and thus two or more of the measured concentrations may include information about the intersected location within the environment. The measurement system 100 may be capable of extracting information (e.g., height 125) about a location, which may include a height, based on information from the two or more intersecting measurements. The measurement system 100 may record (e.g., in memory 128) information about the placement of the measurement light paths (e.g., the positions of the light rays 110 or 111 and/or the location of the mobile platform 114).

In some embodiments, the gas plume 120 may include an anomalous gas, which may differ in amount or concentration from that which may be normally present in the environment of environment 116 (or may normally be at low or trace amounts in the environment of the environment 116). In some embodiments the gas plume 120 may be an environmental hazard, such as methane. In some embodiments, the environment 116 may include a wellsite, a pipeline, a pipeline right-of-way, a landfill, a waste water facility, a feedlot, an industrial site, a waste disposal site, or combinations thereof. The gas source 118 may be a leak, and the gas plume 120 may be emitted from the source 118 at a leak rate. In some embodiments, the flux of the gas plume 120 may be used to determine the leak rate.

The measurement system 100 may generate a spatial distribution (e.g., a map) of the concentration of the gas plume 120. The spatial distribution of concentrations of the gas plume 120 about the environment 116 may be used, for example, to locate a source 118 (e.g., a leak), and/or determine a flow rate of the gas plume 120 out of the source 118. In some embodiments, one or more actions may be taken based on the measurements and/or spatial distribution such as, for example, evacuating an area, measuring an environmental hazard, locating a gas leak (e.g., dispatching one or more personnel to a site indicated by the measurements and/or spatial distribution), determining a possible repair, conducting a repair (e.g. at a location indicated by the measurements and/or spatial distribution), ensuring regulatory compliance, or combinations thereof. Other actions may be taken in other embodiments.

The optical system 102 may provide scanning light and may receive received light from the environment 116. The scanning light may be represented by the light ray 110 and light ray 111. The optical system 102 may direct the light ray 110 along a scan path. The transmitter 106 may provide incident light (e.g., transmitted light), which may interact with (e.g., be redirected by) the scanner 108 to provide the scanning light. The scanner 108 may redirect the emitted light towards the environment 116 to become the light ray 110 or the light ray 111. The scanner 108 may change the angle and/or direction of the light ray 110 over time. In the example embodiment of FIG. 1, the scanner 108 is shown as a rotating angled reflector, however, any scanner may be used. The light ray 110 may represent a first position of the scanner 108, while the light ray 111 may represent a second position of the scanner 108. While a scanner 108 is shown in FIG. 1, it should be understood that in some embodiments, the scanner 108 may not be used. In some embodiments, additional components (e.g., lenses, filters, beam splitters, prisms, refractive gratings, etc.) may be provided in the measurement system 100 to redirect and/or change other properties of the light. While the embodiment described may use an active remote sensor, passive remote sensors may also be used. In this case a pixel array may be used to capture light or thermal radiation from the environment and a beam scanner may not be necessary. In this case, the light ray 110 may be considered to be light or thermal radiation from the environment measured by one or more pixels. Measurement paths may differ in angle and/or displacement due to platform motion and/or pixel selection.

The optical system 102 includes a transmitter 106, which may produce transmitted light. A portion of the transmitted light (which, in some embodiments may be substantially all of the transmitted light) may reach the scanner 108 as incident light. In some embodiments, the transmitter 106 may produce a broad spectrum of light across a range of wavelengths. In some embodiments, the transmitter 106 may produce the transmitted light with a particular spectrum (e.g., a narrow bandwidth centered on a selected wavelength). In some embodiments, the transmitter 106 may include a laser, and the transmitted light may generally be coherent. In some embodiments, the controller 122 may cause the spectrum of the transmitted light to change over time. In some embodiments, the wavelength of the transmitted light may be modulated for WMS. In some embodiments, the wavelength of the transmitted light may be modulated for frequency-modulated, continuous-wave (FMCW) LiDAR.

The optical system 102 may also receive light from the environment 116. The received light may be thought of as a bundle of light rays (e.g., light ray 110) which reach the receiver 112. In some embodiments, the received light may be redirected by the scanner 108 onto the receiver 112. The size of the area from which light rays reach the receiver 112, and the amount of light which reaches the receiver 112, may be dependent on the field of view of the scanning system 100. In some embodiments, the transmitter 106 and the receiver 112 may be packaged together into a single unit. In some embodiments, the transmitter 106 and the receiver 112 may be coaxial with each other. In some embodiments, a single transceiver may be used as both the transmitter 106 and the receiver 112 (e.g. a monostatic transceiver).

The optical system 102 may optionally be mounted on (e.g., supported by) a mobile platform 114, which may move along a direction of motion 130 relative to the environment 116. In some embodiments, the mobile platform 114 may be an aerial vehicle. The mobile platform may be manned (e.g., an airplane, a helicopter) or unmanned (e.g., a drone). In some embodiments, the unmanned vehicle may operate based on remote instructions from a ground station and/or may operate based on internal logic (e.g., on autopilot). In some embodiments, the measurement system 100 may include more than one optical system 102, which may be mounted in multiple locations, such as on multiple mobile platforms 114.

The motion of the optical system 102 along the direction of motion 130 along with the changing angle of the light ray 110 (and area 'seen' by the receiver 112) due to the scanner 108 may cause the light ray 110 follow a scan path. The scan path may generally have a repeating shape (e.g., a helical shape). In some embodiments, without the direction of motion 130 of the mobile platform 114, the light ray 110 may follow a closed path, such as a circle or an ellipse. In these embodiments, the motion of the mobile platform 114 may extend the closed path into the scan path.

The light ray 110 may interact with one or more targets, such as gas plume 120, within the environment 116. In some embodiments, the gas plume 120 may redirect (e.g., by scattering, reflection, etc.) a portion of the light ray 110 back along an optical path leading to the receiver 112. In some embodiments, the light ray 110 may interact with the gas plume 120 (e.g., via absorption or dispersion) and then be redirected along an optical path back towards the receiver 112 by one or more other features of the environment 116 (e.g., the ground, structure 117, vegetation, etc.). In some embodiments, one or more objects in the environment 116 (e.g., the terrain, structures, vegetation, etc.) may act as a backscattering target and may backscatter the light ray 110 back towards the optical system 102. In some embodiments, the gas plume 120 may both redirect the light ray 110 and also modify the scanning light (e.g., may absorb, scatter, transmit, and/or reflect the light ray 110).

A portion of the light ray 110 may return to the receiver 112 as received light after interacting with the gas plume 120 and/or the environment 116. The receiver 112 may include one or more detectors, which may generate a measurement (e.g., of an intensity, wavelength, phase, and/or other property of the light) based on the received light. The measurements may be provided to the computing system 104. The computing system 104 may generate a gas concentration measurement based on the signal from the receiver 112. As the light ray 110 scans across the environment 116, multiple gas concentration measurements may be generated, which may be spatially distributed across the environment 116. The multiple gas concentration measurements may be from different angles with respect to the gas plume 120, and some of the multiple gas concentration measurements may intersect and/or overlap and may include information about the same region. Certain of the measurements may be associated with a region including the gas plume 120, while other measurements may be associated with regions which do not contain the gas plume 120.

The computing system 104 may determine a presence, location, concentration, flow rate and/or other properties of the gas plume 120 based on the measurements. The computing system 104 may use one or more aspects (e.g., wavelength, intensity, and/or phase) of the received light to determine one or more properties (e.g., concentration, content, etc.) of the gas plume 120. In some embodiments, computing system 104 may compare one or more aspects of the emitted light provided by the transmitter 106 to corresponding aspects of the received light. In some embodiments, computing system 104 may direct the controller 122 to modulate the wavelength of the emitted light provided by the transmitter 106, and computing system 104 may determine properties of the gas plume 120 based on wavelength modulation spectroscopy. The computing system 104 may store one or more pieces of information (e.g., measurements, calculated properties, etc.) in the memory 128 and may send and/or receive information with the communications module 124.

The measurement system 100 may determine a flux of the gas plume 120 based on the gas concentration measurements and information about the wind 121. For example, the measurement system 100 may determine a direction of the wind 121 from the image of the gas plume 120, and/or may acquire information about the wind 121 from an external source (e.g., a weather database, one or more anemometers, etc.). The measurement system 100 may determine a region of (relatively) unperturbed flow of the wind 121, which may be located away from features of the environment 116 such as the structure 117 which may interfere with flow of the wind 121. The measurement system 100 may use the gas concentration measurements to determine a vertical statistical moment and/or vertical distribution of the gas concentrations. For example, the measurement system 100 may use multiple measurements from multiple angles to determine the vertical information about the gas concentration.

Determining the vertical statistical moment or vertical distribution includes determining a height of the gas plume 120 and/or a height of a portion of the gas plume 120. The vertical statistical moment may represent an average height, or a height of center of mass of the gas plume 120. The vertical distribution may represent a vertical column of gas concentration measurements, each of which is associated with a height along the vertical column. In some embodiments, the measurement system may determine a vertical statistical moment and/or vertical distribution at a plurality of locations across a plane 123 which intersects the gas plume 120. While FIG. 1 shows a plane that is perpendicular to the wind direction, any surface, including planes that are not perpendicular to the wind direction, may also be used.

The wind 121 in the environment may have a wind speed which varies with height above the ground. In some scenarios, the wind may have a strong relationship with height, which may be non-linear. The measurement system 100 may determine a vertical wind speed profile which is associated with the gas plume 120. The measurement system 100 may determine a gas flux based on vertical information about the gas concentration (e.g., the vertical statistical moment and/or vertical distribution) and the vertical wind speed profile. In some embodiments, a wind speed at a height matching a height of a given gas concentration may be multiplied. In some embodiments, a plurality of such products may be summed across as a plane 123 to determine a flux through the plane. This process may be iterated (e.g. for different planes) to determine multiple measurements of the flux. Other methods of determining the flux may be used in other example embodiments, as described in more detail herein.

The computing system 104 may store one or more executable instructions, and one or more additional pieces of information (e.g., information about the wind 121) in the memory 128. The processor 126 may use the information in the memory 128 along with measurements from the optical system 102 to determine properties of the gas plume 120. The processor 126 may operate the controller 122 to control the measurement system 100 (e.g., by operating the transmitter 106). The computing system 104 may be in communication with one or more remote locations via the communications module 124.

In some embodiments, the processor 126 may determine a spatial distribution of the concentration of the target gas plume 120. The concentration of the gas plume 120 may be determined based on individual measurements which may be swept along the scan path. The processor 126 may measure a spatial location of a given measurement (e.g., based on mapping of the environment 116) and/or may determine the spatial location based on known location parameters (e.g., based on known properties of the direction of motion 130 and/or scan path of the light ray 110). In some embodiments, the measurement system 100 may include one or more location and/or orientation determination system (e.g., a GPS, an inertial navigation system, a range-finding system, etc.) to aid in determining the spatial distribution. The individual measurements may then be combined with the spatial information to generate the spatial distribution. The spatial information may be 2D and/or 3D. While a single processor 126 and memory 128 are shown in FIG. 1, in other examples multiple processor(s) and/or memories may be used—e.g., the processing and storage described herein may be distributed in some examples.

The measurements and/or information derived from the measurements (e.g., a spatial distribution of the measurement) along with other information (e.g., an altitude of the mobile platform 114, an orientation of the scanner 108, etc.) may be provided to the memory 128 and/or communications module 124. The memory 128 may be used to record information and/or store instructions which may be executed by the processor 126 and/or controller 122 to perform the measurements. The communications module 124 may be a wireless communication module (e.g., radio, Bluetooth, Wi-Fi, etc.) which may be used to transmit information to one or more remote stations and/or to receive instructions from the remote stations.

In some embodiments, where a mobile platform 114 is used, one or more components of the measurement system 100 may be located off of the mobile platform 114. For example, components of the computing system 104 such as the memory 128 and/or the processor 126 may be located at a remote station (e.g., a ground station) and may receive information/instructions from and/or provide information/instructions to the optical system 102 via the communications module 124. The computing system 104 may perform different steps (e.g., as described in FIG. 2) at different locations (e.g., some steps may be performed on the mobile platform 114, while other steps are performed remote from the mobile platform 114). Different arrangements or parts of the measurement system 100 between the mobile platform 114 and one or more remote stations are possible in other examples. Although not shown in FIG. 1, in some embodiments one or more additional components may be provided in the measurement system 100 (either in the mobile platform 114 or at a remote location communicatively coupled to the other components) such as a user interface, display, etc. In some embodiments, the measurement system 100 may collect measurements at a first time, and may process the measurements at a later time.

Figure 2:
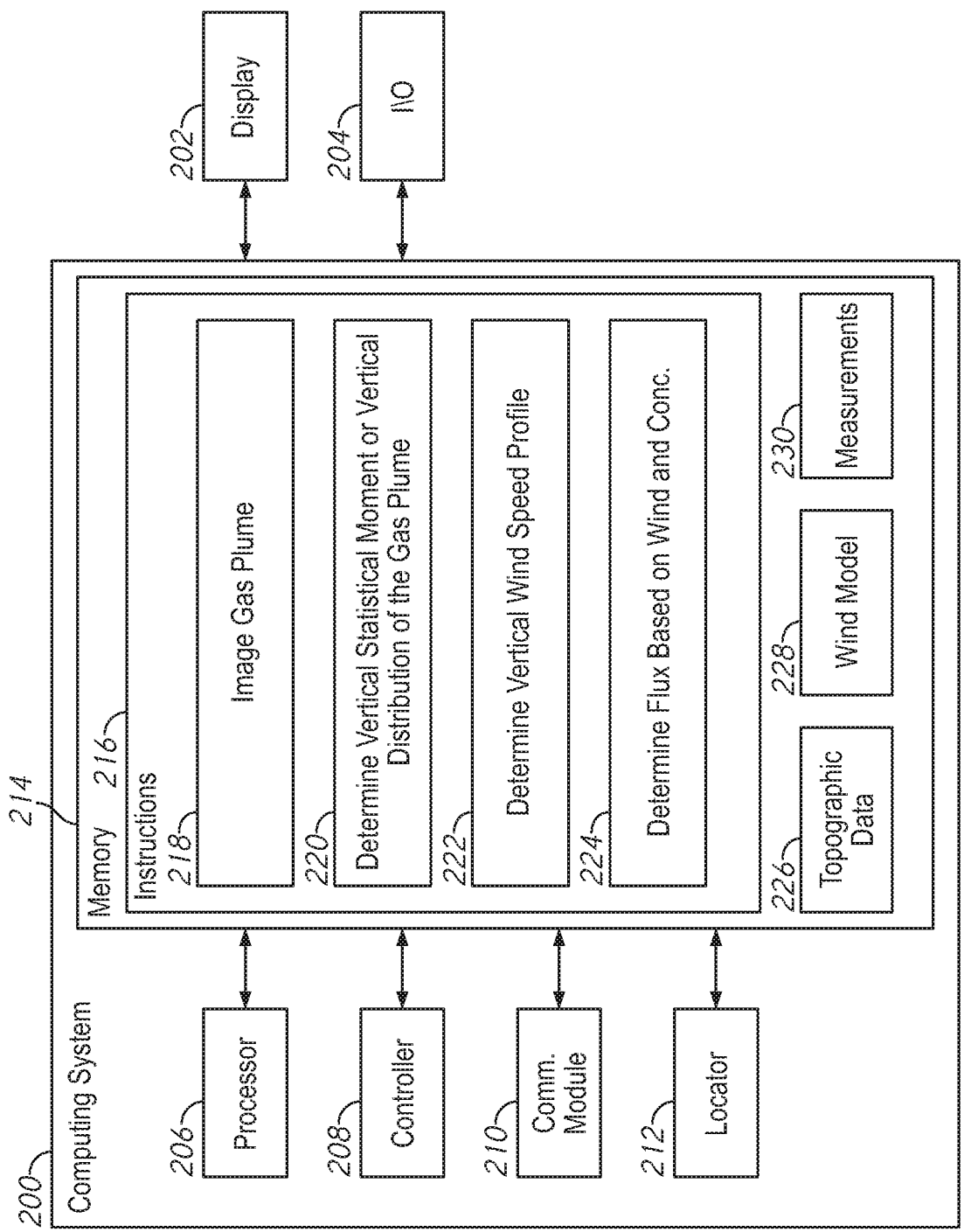
FIG. 2 is a block diagram of a computing system according to an embodiment of the present disclosure.

FIG. 2 is a block diagram of a computing system according to an embodiment of the present disclosure. In some embodiments, the computing system 200 may be used to implement the computing system 104 of FIG. 1. The computing system 200 includes one or more processors 206, a controller 208, a communications module 210 and a locator 212 all coupled to a memory 214. The memory 214 includes instructions 216 which may include particular sets of instructions such as block 218 which includes instructions for imaging a gas plume, block 220 which includes instructions for determining a vertical statistical moment and/or vertical distribution of the gas plume; block 222 which includes instructions for determining a vertical wind speed profile, and block 224 which includes instructions for determining gas flux based on the wind velocity and gas concentrations. The memory 214 may include one or more other components which may be accessed by one or more of the instructions 216, such as topographic data 226, wind model 228, and/or additional measurements 230. The computing system 200 may be coupled to additional components such as a display 202 and an input/output (I/O) device 204 (e.g., keyboard, mouse, touchscreen, etc.).

While certain blocks and components are shown in the example computing system 200, it should be understood that different arrangements with more, less, or different components may be used in other embodiments of the present disclosure. For example, while a single processor block 206 is shown in the computing system 200, multiple processors may be used. In some embodiments, different processors may be associated with different processes of the computing system 200, such as with different instructions 216 in the memory 214, or with different functions (e.g., a graphics processor, flight plan). While the example computing system 200 is shown as a single block, it should be understood that the computing system 200 may be spread across multiple computers. For example, a first computer may be located near the optical system (e.g., a computer on mobile platform 114 of FIG. 1), while a second computer may be at a remote location. The various components of a computing system 200 may be coupled by any combination of wired and/or wireless connections (e.g., cables, wires, Wi-Fi, Bluetooth, etc.). Similarly it should be understood that the instructions 216 may be separated in time as well. For example, certain of the steps (e.g., step 218) may happen at a first time, while other steps (e.g., steps 220-224) may represent post-processing and may occur at a later time.

The processor 206 may access the memory 214 to execute one or more instructions 216. Based on the instructions 216, the processor 206 may process measurements from an optical system (e.g., optical system 102 of FIG. 1). The processor 206 may receive measurements in near real-time from the optical system as the measurements are generated (e.g., measurements may be streamed, provided real-time, or otherwise dynamically transferred), and/or may retrieve measurements 230 which were previously stored in the memory 214. In some examples, the instructions 216 may cause the processor 206 to process the measurements by filtering the measurements, adjusting the measurements, generating new data or flight instructions based on the measurements, and/or storing the measurements in the memory 214. In some embodiments, the processor 206 may process measurements from additional sources, such as from anemometers to measure the wind speed at a given location. In some embodiments, the additional sources may be external to the computing system 200, and the information may be obtained via the communication module 210. For example, wind information may be provided by an online weather forecasting system (e.g., a government database, a commercial system). The memory 214 may include additional information such as mathematical constants and mathematical relationships which may be used by one or more of the instructions 216 when executed by the processor 206.

The instructions 216 may include block 218, which includes instructions for imaging the gas plume. The instructions in block 218 may cause the processor 206 to direct a measurement system (e.g., airborne platform and/or measurement system 100 of FIG. 1) to collect measurements of gas concentration in a target area of the environment. The processor 206 may receive raw measurements from an optical system (e.g., optical system 102 of FIG. 1) and may use the raw measurements to determine a gas concentration. The processor 206 may use information about the measurement to determine the spatial distribution of gas concentrations in the target area. For example, the processor may use information about the angle at which the measurement was taken relative to the measurement system 100 and/or information about the location of the measurement system 100 with respect to the environment.

In some embodiments, the location information may be provided by a locator 212, which may be a system capable of determining a location over time of the measurements (e.g., a GPS). In some embodiments, the measurement system may measure one or more spatial properties of the target area. For example, the measurement system may be able to measure a range to a surface in the target area. The collected range information as the measurement system scans the target area may be used, for example, to generate a topographical map of the target area.

In some embodiments, additional properties of the gas plume may be determined based on the measurements. For example, a location of an origin of the plume (e.g., source 118 of FIG. 1) may be determined based on the plume image. The direction and divergence of the plume may be also be calculated based on the plume image.

Instructions 216 also include block 220, which includes instructions for determining a vertical statistical moment and/or vertical distribution of the gas plume. Once a plume has been imaged (e.g., by the instructions in block 218), the measurements may be analyzed to determine a concentration of the gas and an associated height of the concentration. In some embodiments, the processor 206 may determine a vertical statistical moment of the gas plume. The vertical statistical moment may represent an average height of the gas plume, such as a center of mass of the gas plume. In some embodiments, the processor 206 may determine a vertical distribution of the gas plume, where a plurality of gas concentration measurements are distributed along a vertical column, with associated heights. In some embodiments, the processor 206 may iterate this process to determine a plurality of co-planar vertical statistical moments or vertical concentration distributions. In some embodiments the processor 206 may determine multiple planes worth of vertical statistical moments or vertical concentration distributions.

In some embodiments, the vertical statistical moment of the gas plume may be determined, estimated, or inferred based on topographic information about the environment around the gas plume. For example, if the environment contains a likely source of the gas plume (e.g., the gas is methane and the environment contains a methane storage tank suspected of being leaky) then a height of the gas plume may be inferred based on the suspected height of the leak. More details about determining the height information based on topographical are discussed in FIG. 9.

In some embodiments, the measurement system (e.g., measurement system 100 of FIG. 1) may collect measurements at a plurality of angles with respect to the gas plume. Step 220 may direct the processor 206 to determine the vertical statistical moment and/or vertical distribution of the gas concentration based, at least in part, on the plurality of angles. For example, the measurements may be taken from a first measurement angle and a second measurement angle (e.g., a forward facing angle and a backwards facing angle). The vertical statistical moment may be triangulated based on the first and second angle. Triangulation is discussed in more detail in FIGS. 10-12. In another example, the measurements may be grouped together into forward and backwards looking groups of measurements, which may be used to determine a vertical statistical moment of the gas plume. Sorting the measurements into forward and backward looking sets is described in more detail in FIG. 13.

In some embodiments, the gas plume image may be used to determine a vertical distribution of gas concentrations based on a vertical statistical moment. For example, as previously discussed, the vertical statistical moment may represent a median location or an average (e.g., a weighted average) location such as a centerline (e.g., a center of mass) of the gas plume. The measurement system may determine a horizontal distribution of the gas concentrations. Based on the assumption that the gas plume may generally be cylindrical, the horizontal distribution may be rotated about the centerline and may be treated as a vertical distribution of the gas concentrations.

Figure 14:
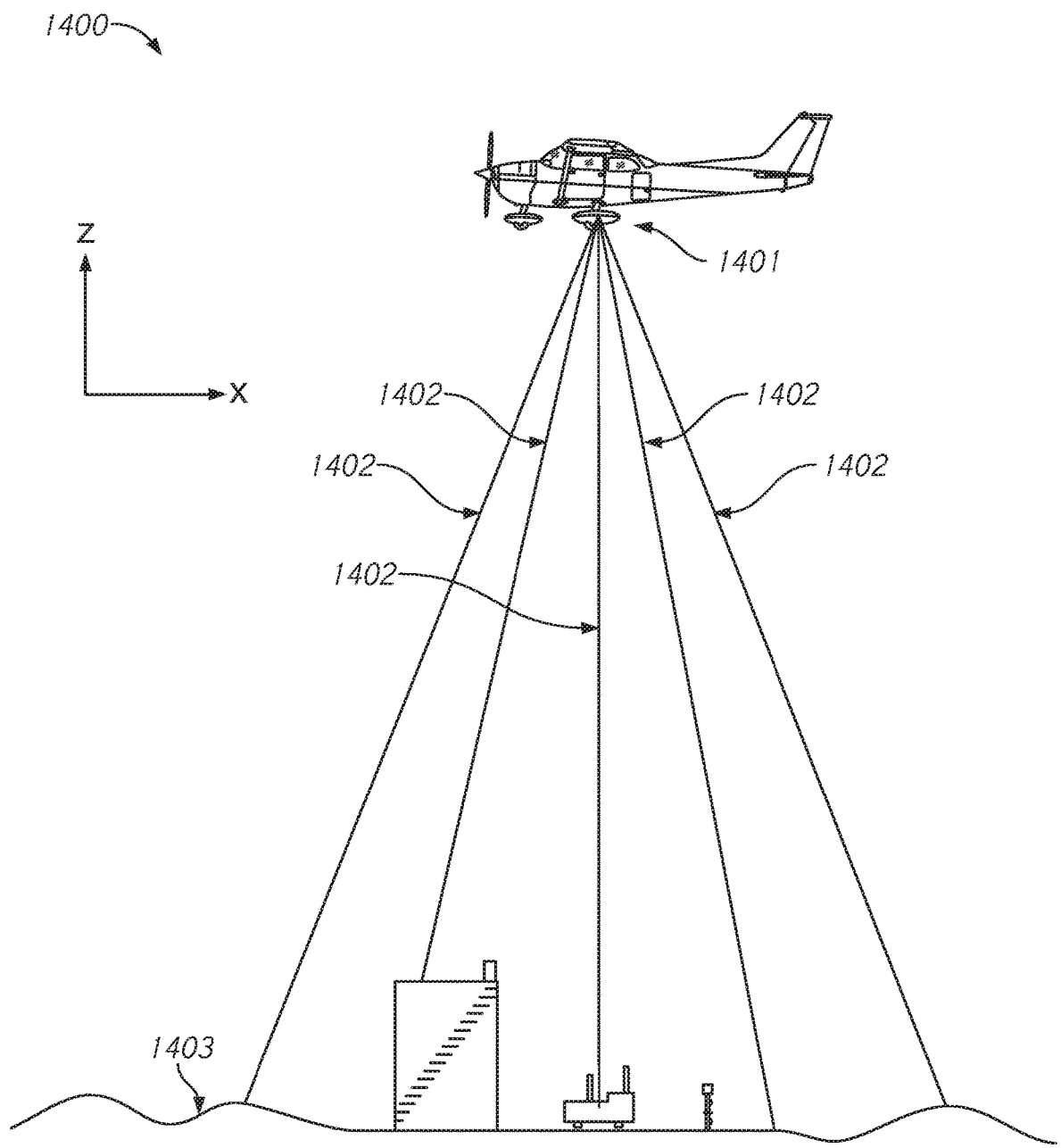
FIG. 14 is a block diagram of a measurement system according to an embodiment of the present disclosure.
Figure 15:
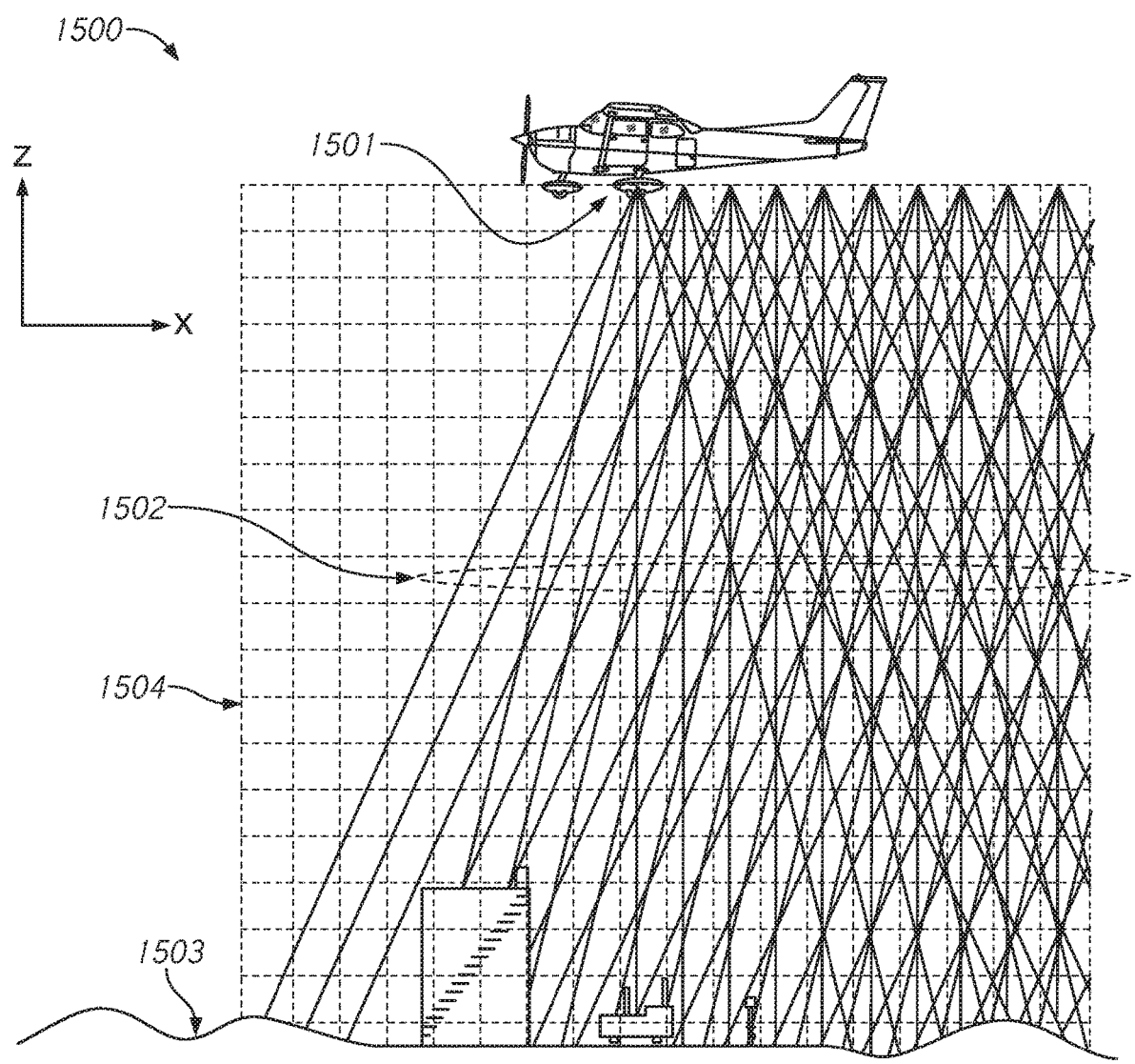
FIG. 15 is a block diagram of a measurement system according to an embodiment of the present disclosure.
Figure 16:
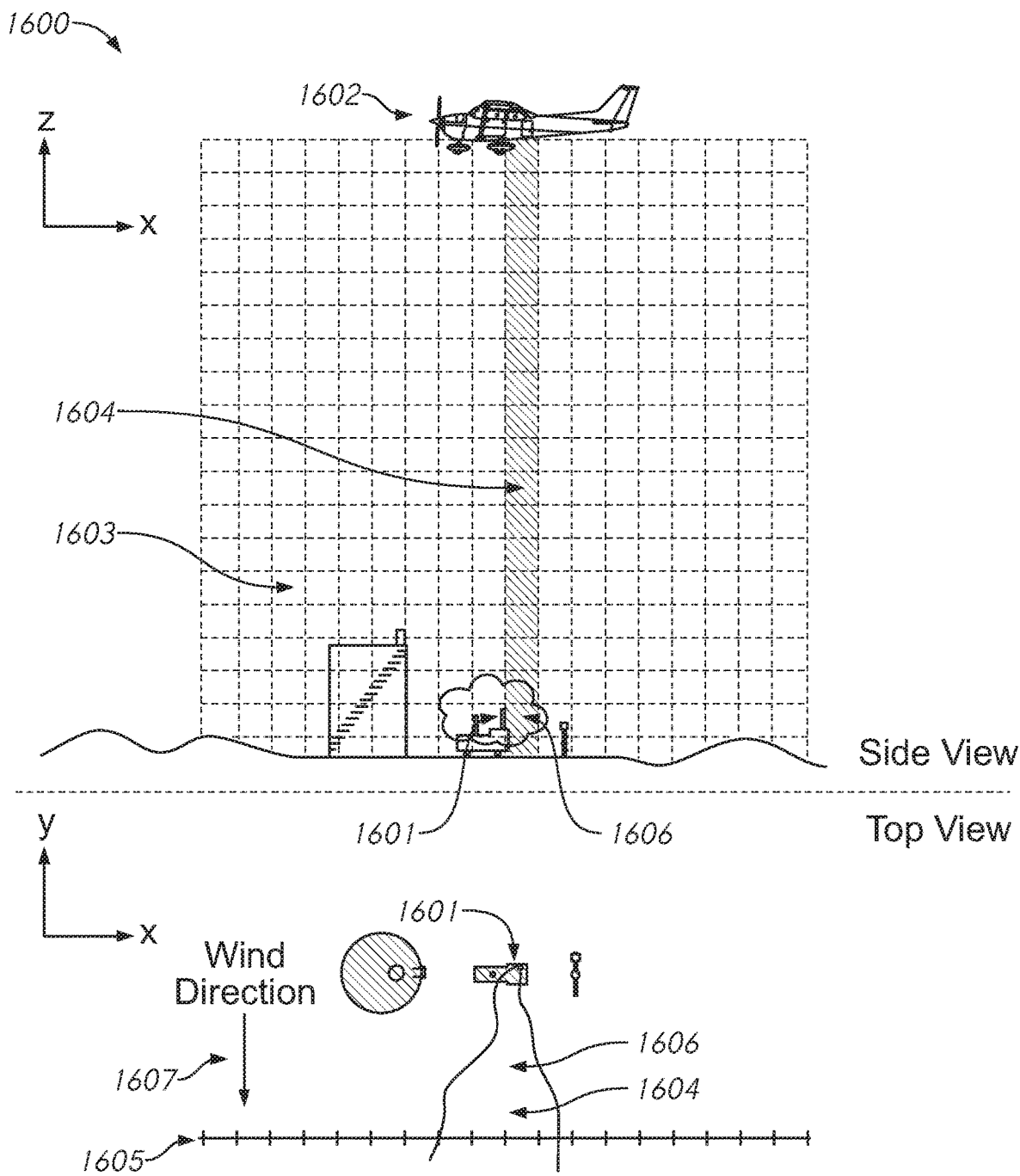
FIG. 16 is a block diagram of a measurement system according to an embodiment of the present disclosure.

In some embodiments, the measurement system may collect measurements from a plurality of angles and positions with respect to the gas plume. A grid may be created and gas concentrations may be assigned to different grid squares based on the plurality of angles and positions of the plurality of measurements. For example, a tomographic inversion algorithm may be used to fill in the grid squares based on the plurality of measurements. A vertical column of the grid cells may then determine a vertical distribution of gas concentrations. FIGS. 14-16 discuss gridding the environment in more detail.

The instructions 216 also include block 222, which includes instructions for determining a vertical wind speed profile. The instructions in block 222 may also involve determining a wind direction and/or determining a region of unperturbed flow of the wind. The wind direction may be determined based on external sources (e.g., weather databases) and/or from the properties of the gas plume image (e.g., the heading of the plume). The processor 206 may determine a vertical wind speed profile associated with at least one location associated with the gas plume. In some embodiments, the vertical wind speed profile may be associated with the region of unperturbed flow. In some embodiments, the vertical wind speed profile may be used to determine a wind speed at an average location of the gas plume, for example a vertical statistical moment of the gas plume. In some embodiments, the vertical wind speed profile may be used to match a wind speed to each of a plurality of gas concentrations in a vertical distribution of the gas concentrations.

In some embodiments, the vertical wind speed profile may be based on wind speed measurements, either from sensors such as anemometers or measurements obtained from weather databases. In some embodiments, the wind speed measurements may be adjusted to match a location associated with the gas plume. For example, the gas plume at the location may be at a gas plume height, while the gas plume (certain points, or moments) may be at a different height. A wind column model may be used to adjust the measurement to match the expected wind speed at the gas plume height. In some embodiments, a plurality of wind speeds may be determined for a plurality of different locations in the gas plume (e.g., different planar cross-sections of the gas plume, different grid cells of the gas plume).

In some embodiments, wind data may be obtained through the communications module 210 from weather modeling services. Weather modeling services combine observations from weather stations around the world with global topographic information and high spatial resolution weather modeling to provide wind speed and direction data at any location on the planet (known as weather model data), effectively filling in the gaps between the weather station locations. Weather modeling services offer wind speed and information at a large number of positions on the globe with reasonable temporal resolution. A variety of wind speed and direction data products may be available in the weather model outputs, such as, for example, average speeds and directions for different specified heights above ground as well as gust speeds different specified heights above ground.

These services may offer archived wind data such that wind speed and direction information for a particular time and location may be retrieved at a later date for post processing. As the accuracy of weather model data improves and the data resolution increases (both spatially and temporally) these services may become increasingly useful for producing accurate and cost-effective gas flux estimates.

In some embodiments, the plume may be emitted from an area of perturbed wind flow. For example, structures around the source of the leak may disturb the flow of the wind, and may cause turbulence, eddies, and/or other currents in the wind. The gas plume may also be emitted from a pressurized source, which may further perturb air flow around the area of the source. The processor 206 may determine a region of the gas plume image with relatively unperturbed wind flow. In some embodiments, the region of unperturbed flow may be identified based on gas concentrations in the plume image. In some embodiments, the region of unperturbed flow may be identified based on topographic information about the environment, which may be measured by the measurement system (e.g., by using the optical system to collect range information) and/or may be based on existing topographical or camera data.

Once a region of unperturbed flow has been identified, the processor 206 may select one or more locations within the region. In some embodiments, these locations may be planes which are perpendicular to the direction of the wind. The orientation of the planes may be based on the wind direction determined from the gas plume image. The processor 206 may determine a gas concentration spatially distributed in the plane. The spatially distributed gas concentration may be combined with spatially distributed wind speeds to determine gas flux. In some embodiments, the processor 206 may filter the measurements, such that measurements outside the region of unperturbed flow are discarded, while measurements inside the region of unperturbed flow are retained. Such filtering may, for example, occur after block 218 but before blocks 220-224.

The instructions 216 may also include block 224, which may be executed by the processor 206 to determine a flux of the gas. The gas flux may be determined based on both the gas concentration information from block 220 and the wind speed information from block 222. For example, a flux may be determined along a plane. In some embodiments, the plane may be perpendicular to the wind direction. In some embodiments, the plane may be located in the region of unperturbed flow. In block 220, one or more gas measurements may be determined with a particular height in the plane. For example, there may be vertical columns of gas distributions across the plane and/or gas concentration measurements associated with a vertical statistical moment in the plane. Each vertical slice may have a flux determined by multiplying the gas concentration by a wind speed associated with the height of the gas concentration and possibly integrating along the vertical slice. The flux through the plane may then be determined by summing fluxes of vertical slices across the plane. In some embodiments, the block 224 may be executed to determine an overall flux of the gas. For example, the overall flux may indicate a leak rate of the gas from the source of the gas. In some embodiments, block 224 may be executed to determine flux through a plurality of different areas (e.g., planar cross sections) of the gas plume.

In some embodiments, blocks 218-224 may be repeated by the instructions 216. The gas flux at a plurality of locations may be determined. In some embodiments, an overall gas flux may be determined based on a combination of several different flux measurements. In some embodiments tomographic cross sections may be computed, and the gas flux through a plurality of the cross sections may be calculated.

The computing system 200 may also be coupled to be one or more external components, such as a display 202 and an input/output device (I/O) 204. In some embodiments, the display 202 may be used to display one or more pieces of information, such as a gas plume image, which may take the form of a map of the gas concentration measurements in space. In some embodiments, the gas plume image may be overlaid on a representation of the environment (e.g., an aerial image of the environment, a map of the environment, topographic information about the environment, etc.). In some embodiments, the I/O 204 may allow a user to control one or more operations of the computing system 200. For example, the user may be able to select a source of the wind speed measurements (e.g., from different sensors and/or from different external services).

Figure 3:
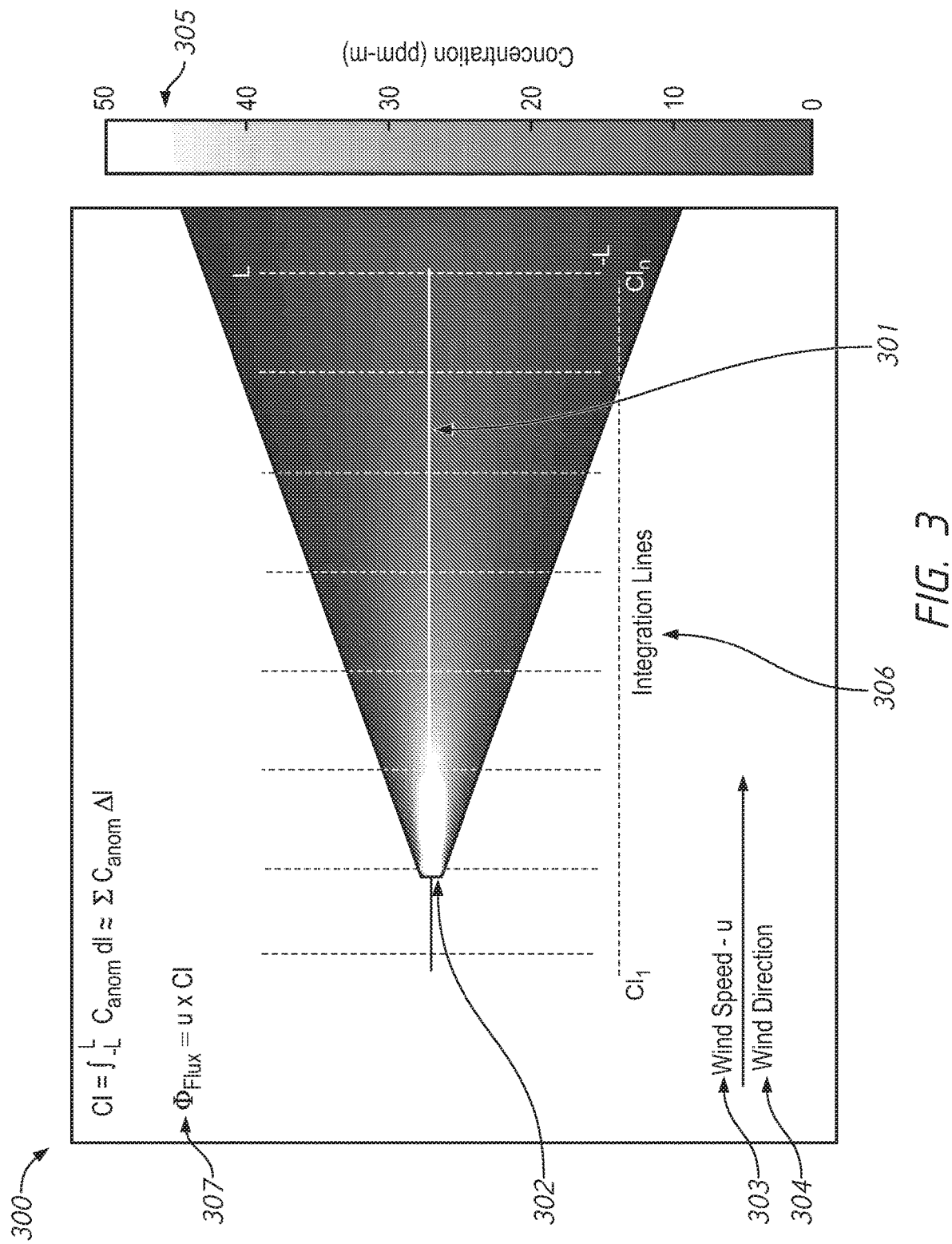
FIG. 3 is a gas plume image according to an embodiment of the present disclosure.

FIG. 3 is a gas plume image according to an embodiment of the present disclosure. The gas plume image 300 may be a gas plume image acquired by the measurement system 100 of FIG. 1 and/or processed by the computing system 200 of FIG. 2 in some embodiments. The gas plume image 300 may be acquired and/or processed by an implementation of one or more of the blocks 218-224 of FIG. 2. The x and y axis of the gas plume image 300 represent distance along orthogonal axis of the environment as seen from above (e.g., the y-axis may represent North/South, while the x-axis may represent East/West). The intensity or shading of the pixels at any given point in the gas plume image 300 represent the measured concentration of gas at that point. The gas plume image 300 may represent a slice through a particular height of the gas plume or may represent vertical path-averaged or path-integrated gas concentration measurements.

The gas plume image 300 includes a gas plume 301 which is emitted from a source 302. The gas emitted from the source 302 may be blown into a plume 301 by a wind speed (u) 303 blowing along a wind direction 304. As discussed in more detail herein, the wind speed 303 and wind direction 304 shown in the gas plume image 300 may represent an average wind speed 303 and wind direction 304 at a location associated with the gas plume 301. Similarly, the wind speed 303 and wind direction 304 may represent the wind speed and direction at a particular height. The actual wind speed 303 and direction 304 may vary at different locations in space.

The shade map 305 indicates the gas concentration at points in the image, with lighter shading representing higher concentrations of gas. The shading map 305 shown in the example of FIG. 3 shows an example scale of gas concentrations, however in other examples other scales of gas concentration may be used. The gas plume image 300 also includes integration lines 306 which may be used to determine an amount of the gas (e.g., a concentration integral), CIi, along an ith one of the integration lines 306. Determination of the wind direction 304 as well as the placement and orientation of the integration lines 306 will be discussed in more detail in FIGS. 4-6. Determination of the wind speed 303 at a location and height associated with the gas plume 301 will be discussed in more detail in FIGS. 7-16.

The amount of gas along the integration lines 306 along with the wind speed 303 may be used to determine a flux at the integration line 306. The flux $\Phi_{flux}$ may be determined based on equation 1, below:

$$\Phi_{flex} = u * CI \qquad \text{Eqn. 1}$$

where u is the wind speed 303 at the height of the integration line 306 and CI is the concentration integral along the integration line 306. The concentration integral may be given by equation 2, below:

$$CI = \int_{-L}^{L} C_{anom} dl \approx \Sigma C_{anom} \Delta l \qquad \text{Eqn. 2}$$

where $C_{anom}$ is a measure of the gas concentration. The example gas concentration measurement, $C_{anom}$, used in equation 2 may be the anomalous gas concentration, which may be determined as the measured path-integrated gas concentration minus the nominal path-integrated atmospheric concentration of the gas being measured. Other measures of gas concentration may be used in other examples. L is the length along the integration lines 306 from the centerline of the gas plume in both the positive and negative direction (e.g., the total length of each integration line 306 is 2 L) and dl is the incremental distance along the integration line 306. As also shown in equation 2, the concentration integral, CI, may be approximated as a sum of all the concentration measurements along a given integration line 306 multiplied by $\Delta l$, the spacing between each measurement along the line. By substituting Equation 2 into Equation 1, the flux $\Phi_{flux}$ may be given by Equation 3, below:

$$\Phi_{flux} = u \Sigma C_{anom} \Delta l \qquad \text{Eqn. 3}$$

Since equation 3 depends on both the wind speed and the gas concentration measurements, the overall accuracy of the flux may be based on the accuracy of the gas concentration measurements and the accuracy of the wind speed associated with those measurements. It may be desirable to increase the accuracy of the flux by increasing the accuracy of the gas measurements and/or the wind speed associated with the measurements. Equation 3 may be most accurate in cases where the wind speed and direction are relatively uniform across the integration line. This condition may not be met in regions close to the emission source where objects, such as storages tanks, separators, incinerators, well heads, derricks or other equipment may alter the wind field.

In some embodiments, to optimize the accuracy of flux estimates produced by equation 3 it may be desirable to identify regions of the gas plume where the wind field is unperturbed by, for instance, complex topography or dynamics associated with a pressurized leak. Regions corresponding to unperturbed wind flow may be regions where the wind field has low perturbations due to physical obstructions, dynamics associated with a pressurized leak, or other cause leading to non-uniform flow. In some embodiments, a region of unperturbed flow may be determined based on the gas plume images. In some embodiments, a region of unperturbed flow may be determined based on topographic information about the environment.

In some embodiments, local wind speed and direction estimates may be combined with 3D topographic information to produce an improved estimate of the wind field near a gas plume. This capability may be particularly useful for leaks located near complex terrain or infrastructure (e.g., where a region of unperturbed flow is difficult to locate). Topographic information may be acquired from 3D lidar data (e.g., as acquired by the measurement system 100 of FIG. 1), and/or from other sources (e.g., pre-existing topographic maps). The wind and topography data may be inputted as boundary conditions into a computational fluid dynamics (CFD) simulation to estimate a wind velocity vector field in the vicinity of the plume. Such simulations can be performed using a number of CFD software packages, for example commercially available and/or open source packages. The resulting wind velocity vector field outputted by the CFD simulation may then be used to derive an improved accuracy flux estimate in a more general form of Equation 3, as given by Equation 4, below, $$\Phi_{flux} = \Sigma C_{anom}(\hat{n} \cdot \vec{u}) \Delta l \qquad \text{Eqn. 4}$$

where $\hat{n}$ is the unit vector normal to the surface where the gas concentration is being measured and $\vec{u}$ is the velocity vector at the location of a gas concentration measurement.

Figure 4:
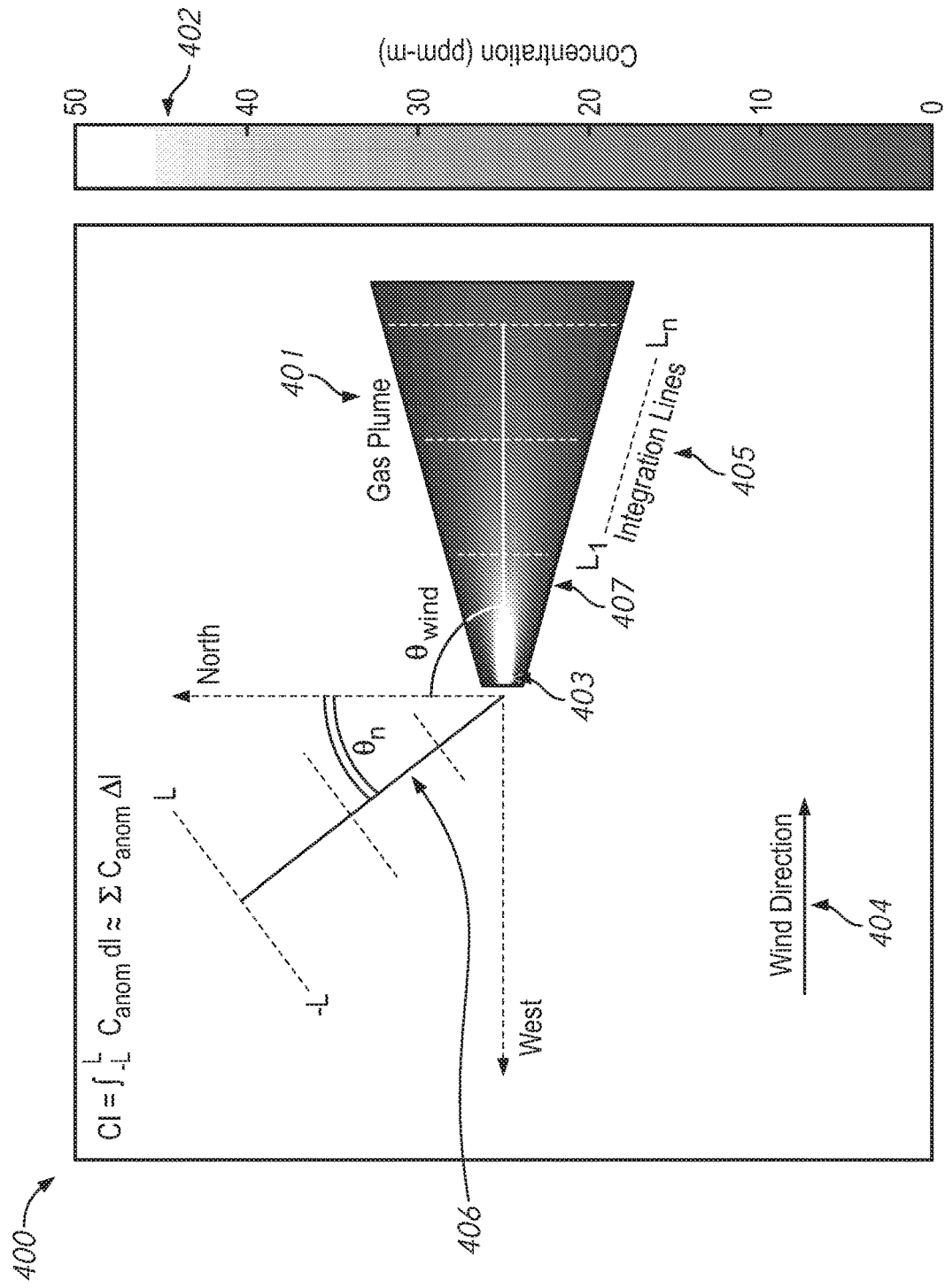
FIG. 4 is a gas plume image according to an embodiment of the present disclosure.
Figure 5:
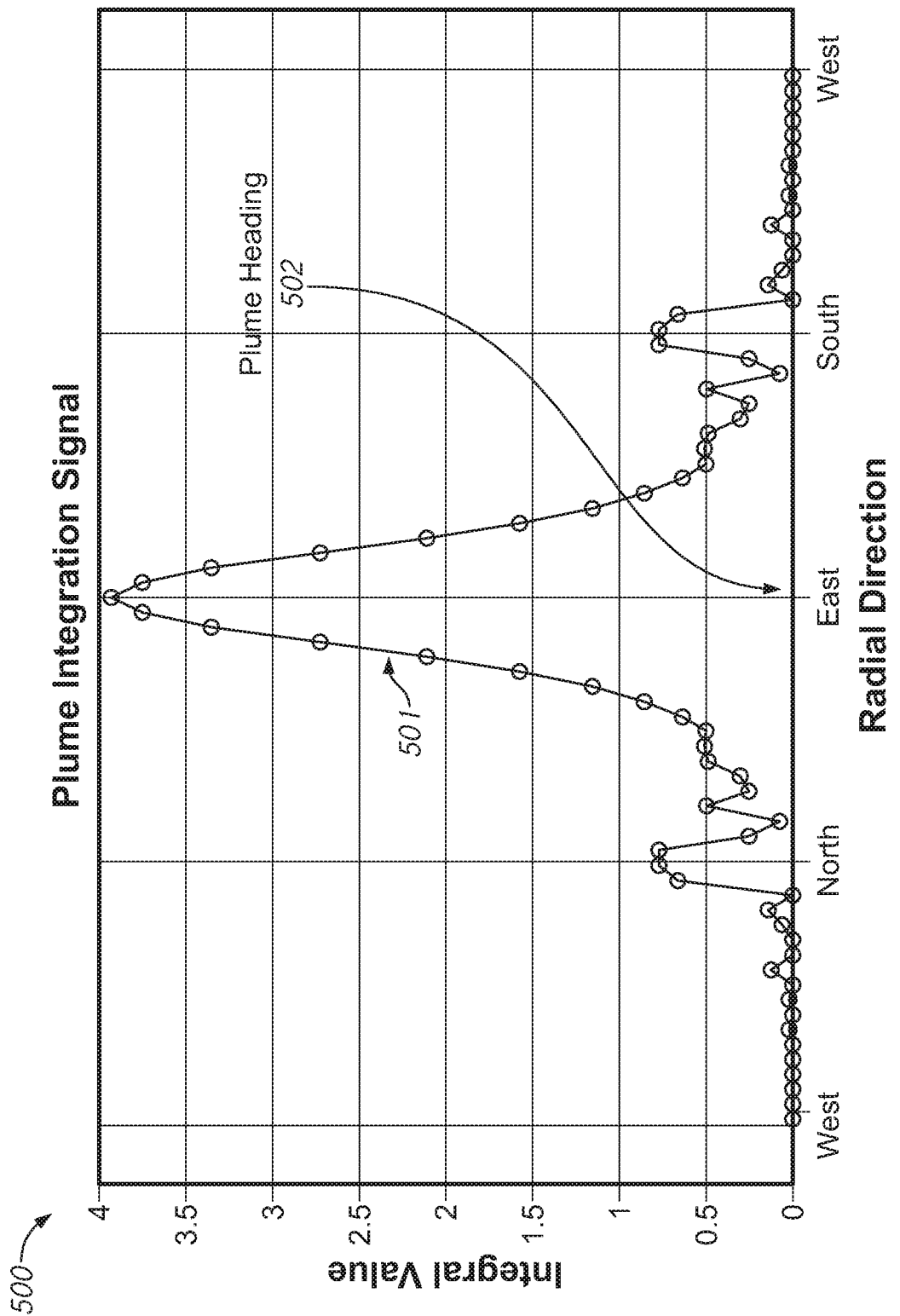
FIG. 5 is a graph showing gas concentration versus direction according to an embodiment of the present disclosure.

FIGS. 4 and 5 show examples of methods that may be used to determine the heading (e.g., direction) of the gas plume based on the gas concentration data in the gas concentration image. In some embodiments, FIGS. 4 and 5 may be implemented by the computing system 200 of FIG. 200 using measurements from the measurement system 100 of FIG. 1. Once the heading of the gas plume has been determined, it may be useful for determining a variety of other factors useful for determining the flux. For example, since it may generally be expected that the gas plume is primarily influenced by the wind, the heading of the plume may indicate an average direction of the wind. This may be useful for positioning integration lines perpendicular to the direction of the wind (e.g., as described in regards to FIG. 3). As another example, once the heading is known, it may be possible to determine properties of the gas plume along the wind direction, such as flux along the wind direction, which may be useful for determining an area of unperturbed wind flow as described in more detail in FIG. 6. In some embodiments, the wind direction may be known based on measurements and/or weather modeling, and it may not be necessary to determine the plume heading. In some embodiments, a known wind direction may be combined with information from determining the plume heading.

FIG. 4 is a gas plume image according to an embodiment of the present disclosure. The gas plume image 400 depicts a method of determining properties of the gas plume 401 within the gas plume image 400. Gas plume 401 is shaded according to concentration shade map 402, originates from emission location 403 and moves along wind direction 404. Determining the heading (e.g., the direction) of the gas plume 401 may involve computing gas concentration line integrals along numerous integration lines 405 at different distances from emission location 403, and/or computing the average gas concentration within an area 407 relative to emission location 403. Similar to the gas concentration image 300 of FIG. 3, the gas plume image 400 shows orthogonal directions along the x and y axis, and concentration represented as the shading of the pixels. While a certain scale of gas concentration is shown in the example gas plume image 400, other values of concentration may be used in other examples.

The concentration integral or average gas concentration computation may be performed along a variety of radial directions 406 relative to detection location 403. The results of the concentration computations along each direction 406 may be summed to produce graph representing the gas concentration as a function of direction (see, for example, FIG. 5). The concentration may be determined by taking an integral along integration lines (e.g., as described in Equation 2) and/or in an area extending away from the origin of the gas plume 401. The integration lines 405 or area shape 407 may be oriented perpendicular to a line extending radially from emission location 403, and the length of the lines 405 or width of the shape 407 may depend on the radial distance from detection location 403. In some embodiments, the length of the lines 405/width of the shape 407 may increase with increasing distance from the emission location 403. In some embodiments, the concentration may be determined up to a set distance away from the emission location 403. In some embodiments, a filter function may be applied to the area 407, such as a Gaussian plume function, before integrating the gas concentration over area 407.

FIG. 5 is a graph showing gas concentration versus direction according to an embodiment of the present disclosure. The graph 500 shows a concentration integral versus radial direction curve 501 for the gas plume 401 shown in FIG. 4. The graph 500 shows radial direction about the origin along the x-axis, and the value of the integral of gas concentration taken along that direction along the y-axis. While the values of the y-axis shown are arbitrary, it should be understood that any units may be used for the y-axis and any coordinate system may be used for the x-axis.

The concentration integral versus radial direction curve 501 exhibits a peak along the plume heading 502, which may be used to indicate the wind direction at the plume location at the time the gas concentration image was acquired. In some embodiments where wind speed and direction information is available from multiple sources, it may be possible to improve the accuracy of the associated gas flux estimates by combining wind data using an average (e.g., a weighted average) of the multiple sources to derive an improved accuracy wind speed estimate.

Figure 6:
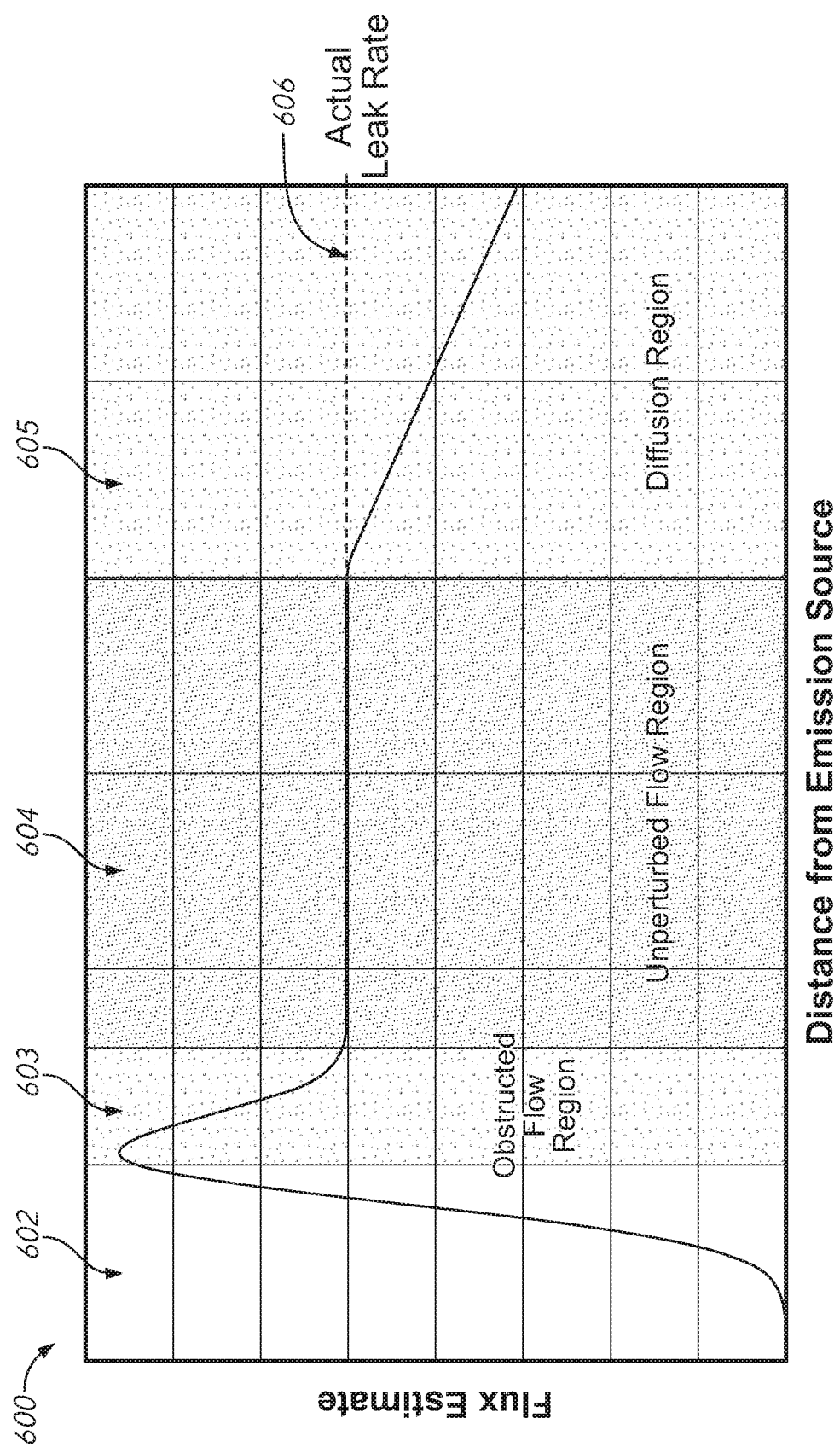
FIG. 6 is a graph showing an example of flux as a function of distance according to an embodiment of the present disclosure.

FIG. 6 is a graph showing an example of flux as a function of distance according to an embodiment of the present disclosure. The graph 600 shows example behavior of a gas plume as it is blown by wind away from a source. The graph 600 may represent a method performed by the computing system 200 of FIG. 2 and may be based on measurements collected with the measurement system 100 of FIG. 1. The y-axis of the graph represents gas flux at points in the plume along a line extending down the center of the plume and parallel to the wind direction (e.g., as determined in FIG. 3), while the x-axis represents displacement along that line. The wind direction may be based on the plume heading (e.g., as determined in FIGS. 4-5). The dashed line 606 represents the rate at which the gas is being emitted into the environment (in this case being leaked by a piece of faulty equipment). It should be understood that the curve shown in the graph 600 is for explanation purposes only, and that real gas plumes may have different behavior.

The graph 600 includes a curve 601 which shows the gas flux as a function of distance. The points along the curve 601 may be determined using Equation 3, by summing concentrations along different integration lines and multiplying by a wind speed. The graph 600 may be divided into four general regions, each of the regions defined by their location along the x-axis. The upwind region 602 is located upwind of the emission source and may contain small amounts of gas due to diffusion and back flow of the wind field caused by objects (typically infrastructure) in the measurement scene. The obstructed flow region 603 may contain obstructed wind flow due to the objects in the scene. In this region, gas imagery may reveal elevated gas concentrations (and hence elevated flux estimates) compared to the actual leak rate as gas near objects may tend to move slower on average than the unperturbed wind velocity. It may also be possible to calculate reduced gas concentration (and hence reduced flux estimates) compared to the actual leak rate in cases where significant portions of the gas plume are obstructed from the gas imagery by objects in the scene. Once an unperturbed flow region 604 is determined, gas concentration measurements may be filtered so that only measurements within the region of unperturbed flow are retained. In some embodiments, one or more particular locations within the region of unperturbed flow 604 may be chosen and the gas flux in those particular locations may be determined.

The unperturbed flow region 604 may typically be located downwind of the objects near the source of the gas plume and corresponds to relatively unperturbed wind flow. This may be the region of the plume that is most likely to produce accurate flux estimates that are in close agreement with the actual leak rate 606. Identification of regions of unperturbed flow may be achieved, for instance, by analyzing the flux estimate versus emitter distance curve (601) for regions of relatively constant flux estimates as a function of distance from the emission source. Finally, in the diffusion region 605 the flux estimates may begin to diminish as a portion of the gas diffuses outside of the region defined by the integration lines.

As may be seen from the graph 600, the calculated gas flux may most reliably measure the true leak rate 606 in the region of unperturbed flow 604. Accordingly, it may be important to identify a region of unperturbed flow 604, so that determination of the flux rate may be performed in the region of unperturbed flow 604. Flux estimates performed at different distances from the emission source in the unperturbed flow region may be averaged to produce an improved accuracy flux estimate.

In some embodiments, a region of unperturbed flow 604 may be identified by calculating the flux at different distances from the source (e.g., by generating a graph similar to the graph 600) and locating a region where the flux is relatively invariant with distance (e.g., by finding a region where the derivative of the flux is low).

In some embodiments, regions of unperturbed wind flow 604 may also be identified by analyzing 3D topographic data to determine regions of the gas plume that are free of objects that may obstruct the wind field. The 3D topographic data may be collected by the same system which provided the gas plume image (e.g., by laser range finding) and/or may come from outside sources (e.g., mapping software). The topographic data may be analyzed to determine a region of relative flatness, which may be identified as a region of unperturbed flow 604. Determination that the plume height is substantially above structures, for instance, may also be used to identify a region of unperturbed flow 604.

Figure 7:
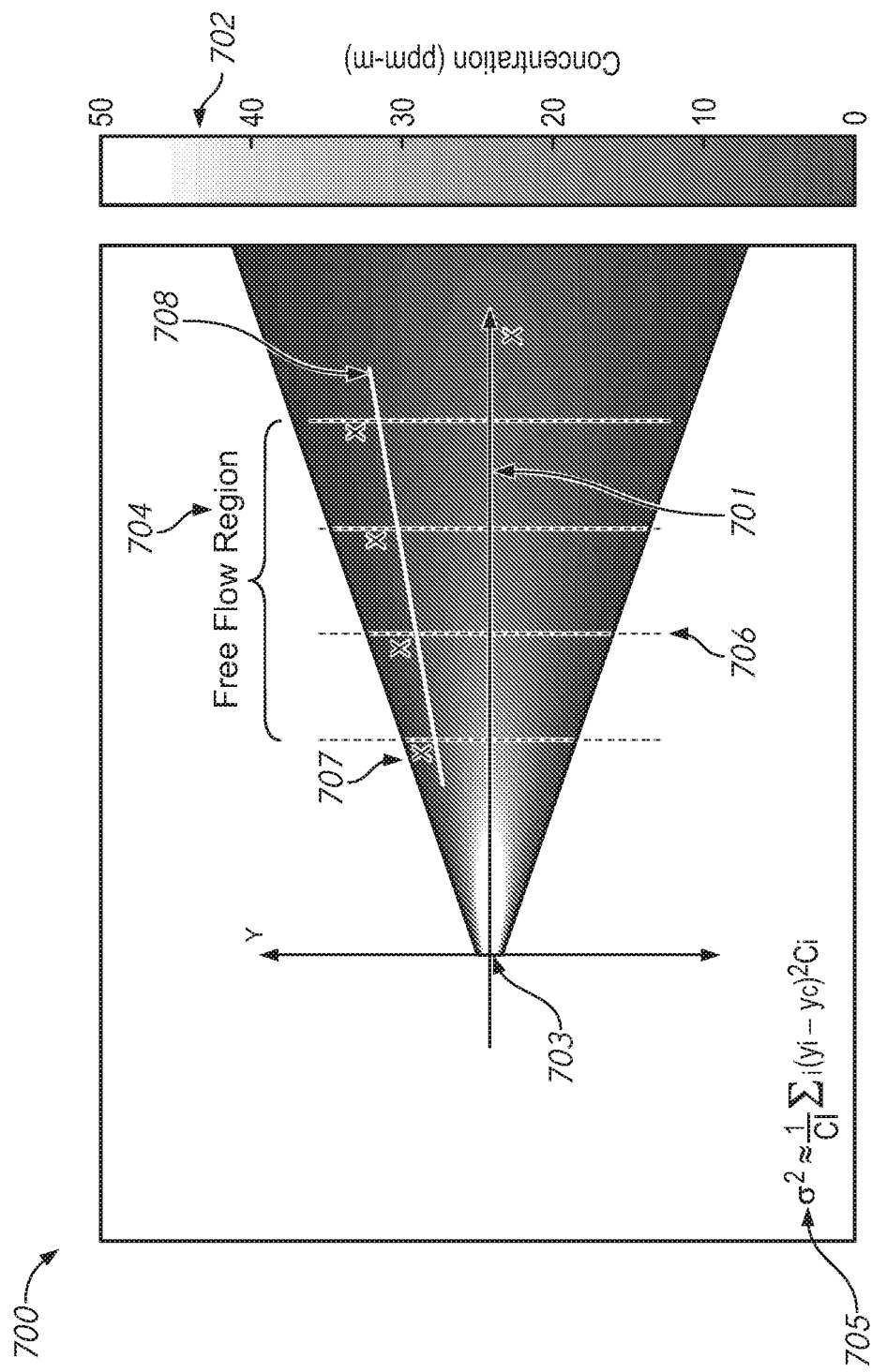
FIG. 7 shows a gas plume image according to an embodiment of the present disclosure.

FIG. 7 shows a gas plume image according to an embodiment of the present disclosure. FIG. 7 shows a particular method of determining wind speed based on the gas plume images, which may be useful when wind speed data is not available. As may be seen from Equation 3, the wind speed may be important for determining the flux. However, accurate wind speed data may not be easily measured or readily available. Once gas concentration as a function of space (e.g., in an area of unperturbed flow) is determined (e.g., as described in FIG. 6), a wind speed measurement may be avoided by analyzing the shape of the plume and optionally by incorporating estimates of local meteorological conditions. This method may be based on relationships between atmospheric turbulence, meteorological conditions and/or wind speed. The method described in FIG. 7 may be implemented by the computing system 200 of FIG. 2, and may be based on measurements collected with the measurement system 100 of FIG. 1.

An example procedure for using plume imagery to determine the wind speed at a particular height may comprise measuring the gas plume divergence angle using gas concentration images. The gas concentration images may be acquired by the measurement system 100 of FIG. 1, or by any other apparatus or method. In some embodiments, the gas concentration images may be filtered so that only data from regions of unperturbed flow is used in subsequent analysis. The example procedure may also include using the plume divergence angle to determine the turbulent diffusion type at the gas plume location. The method may also include using the determined turbulent diffusion type and local weather observations to inferring the wind speed at the gas plume location without actually measuring the wind speed.

The gas plume image 700 represents a slice through gas plume 701 along a particular height. A height distribution of the wind may be found by repeating the process described herein for a plurality of different slices at different heights through the gas plume. Gas plume 701 is shaded according to concentration color map 702 and originates from emission location 703. The divergence angle may be measured by computing the variance ($\sigma^2$) of gas concentration distribution along lines 706, which may be perpendicular to the plume propagation direction, at different positions (x) along the plume propagation direction. The variance along each line 706 may be computed according to Equation 5, below:

$$\sigma^2 = \frac{\Sigma_i(y_i - y_c)^2 c_i}{\Sigma_i c_i} \qquad \text{Eqn. 5}$$

where $C_i$ is the gas concentration measurement at the $i^{th}$ pixel along a given one of the lines 706, $y_c$ is the y-direction mean location of the plume along each line 706 and $y_i$ is the position of concentration measurement $C_i$ along lines 706.

The variance may be computed within a region of the gas plume corresponding to unperturbed wind flow, which may be identified using techniques like the ones discussed in regard to FIG. 6. The computed standard deviation ($\sigma$) along each line 306 may be fitted to a line given by equation 6, below and the slope (m) may be used to determine the divergence angle ($\theta$) as given by equation 7, below:

$$\sigma(x) = mx + \sigma_0 \qquad \text{Eqn. 6}$$

$$\theta = \tan^{-1} m \qquad \text{Eqn. 7}$$

In some embodiments, the plume divergence angle ($\theta$) may be used to determine the turbulent diffusion type of the atmosphere in the gas plume vicinity. In some embodiments, tables and/or other reference materials may be used to determine the turbulent diffusion type based on the plume divergence angle. The atmospheric turbulent diffusion type at the plume location may be combined with meteorological observations to estimate the wind speed at the plume location. In some embodiments, standardized tables may be used to look up the wind speed based on the turbulent diffusion type. In some embodiments, determining a surrogate wind speed based on the atmospheric turbulent diffusion type may require observations of the insolation and cloud cover conditions at the location of the gas plume.

In some embodiments, the methods for avoiding a wind speed measurement may depend on the environment containing the gas plume. For example, the plume divergence method may perform best in open terrain at distances of less than 1 km from the emission source and plume heights of less than 100 m. Other methods of estimating wind speed (for example, as described in FIGS. 8-16) may be used in scenarios outside of this range.

FIGS. 8-16 discuss example methods of adjusting wind speed measurements to match the height of the gas plume. Any of the methods described in FIGS. 8-16 may be implemented on the computing system 200 of FIG. 2, and may be based on measurements collected by the measurement system 100 of FIG. 1. The methods described in FIGS. 8-16 may be used to determine a vertical statistical moment or vertical distribution of the gas concentrations, and may implement step 220 of FIG. 2 in some embodiments.

Figure 8:
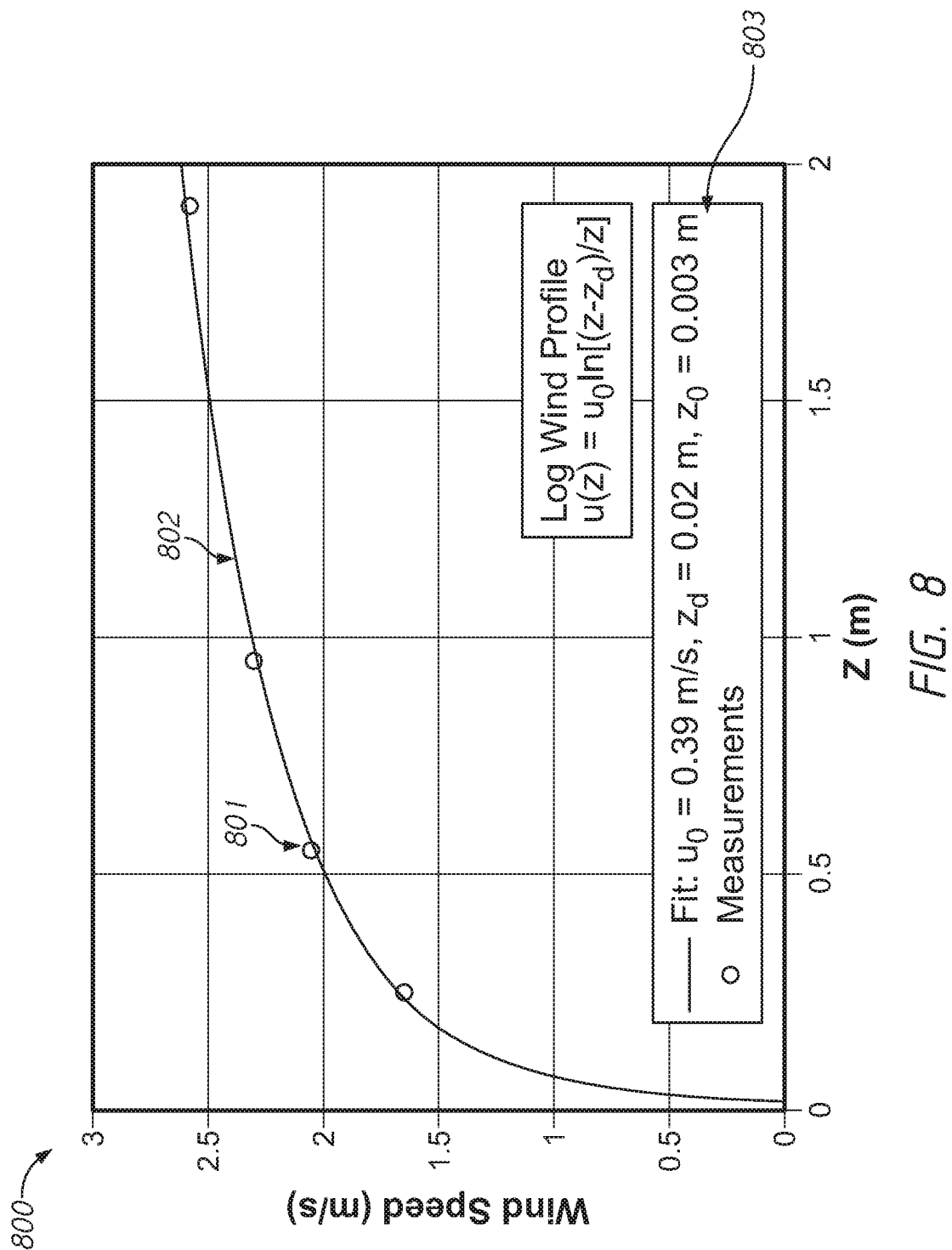
FIG. 8 is a graph of a vertical wind speed profile according to an embodiment of the present disclosure.
Figure 9:
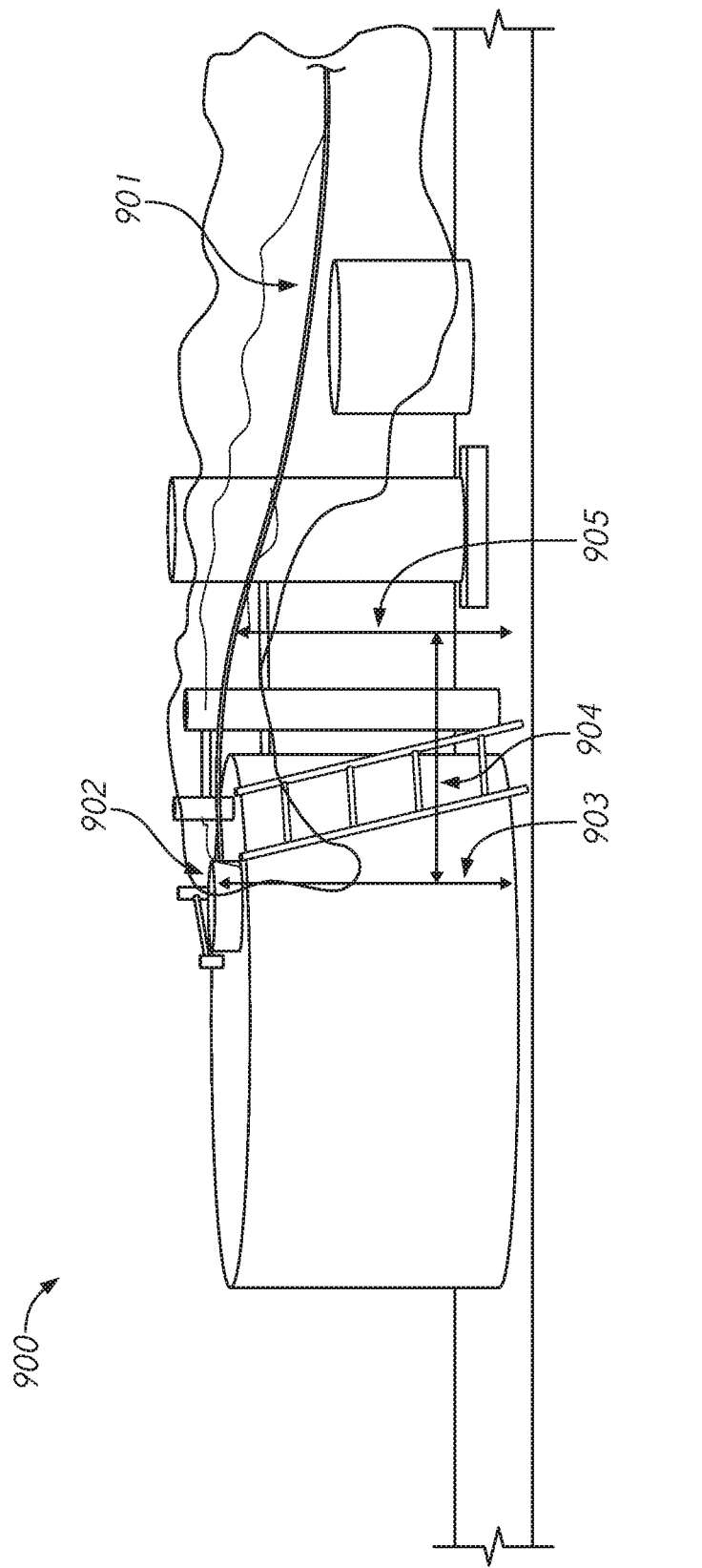
FIG. 9 is a block diagram showing a gas plume in an environment according to an embodiment of the present disclosure.
Figure 10:
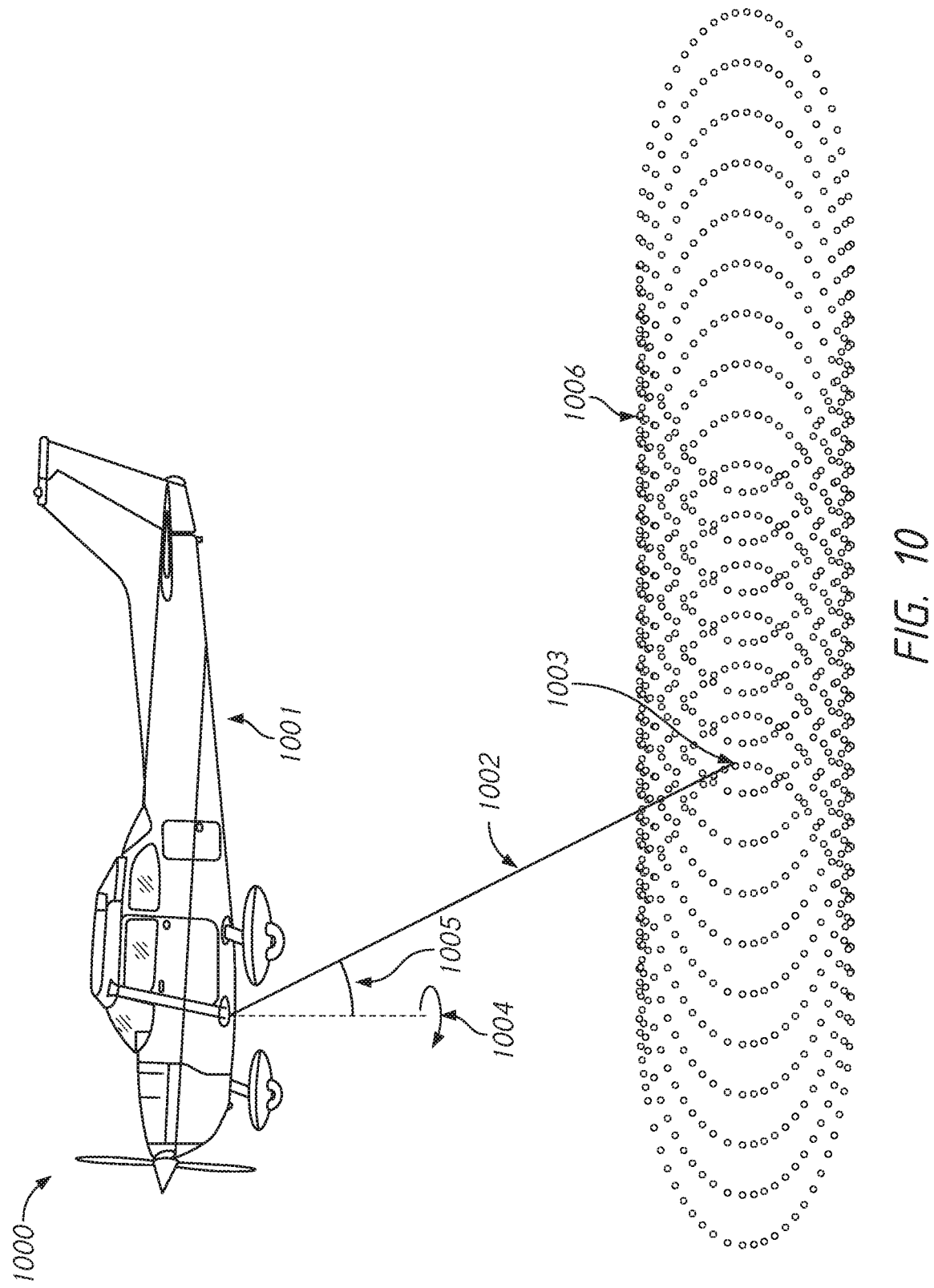
FIG. 10 is a block diagram of an example measurement pattern according to an embodiment of the present disclosure.
Figure 11:
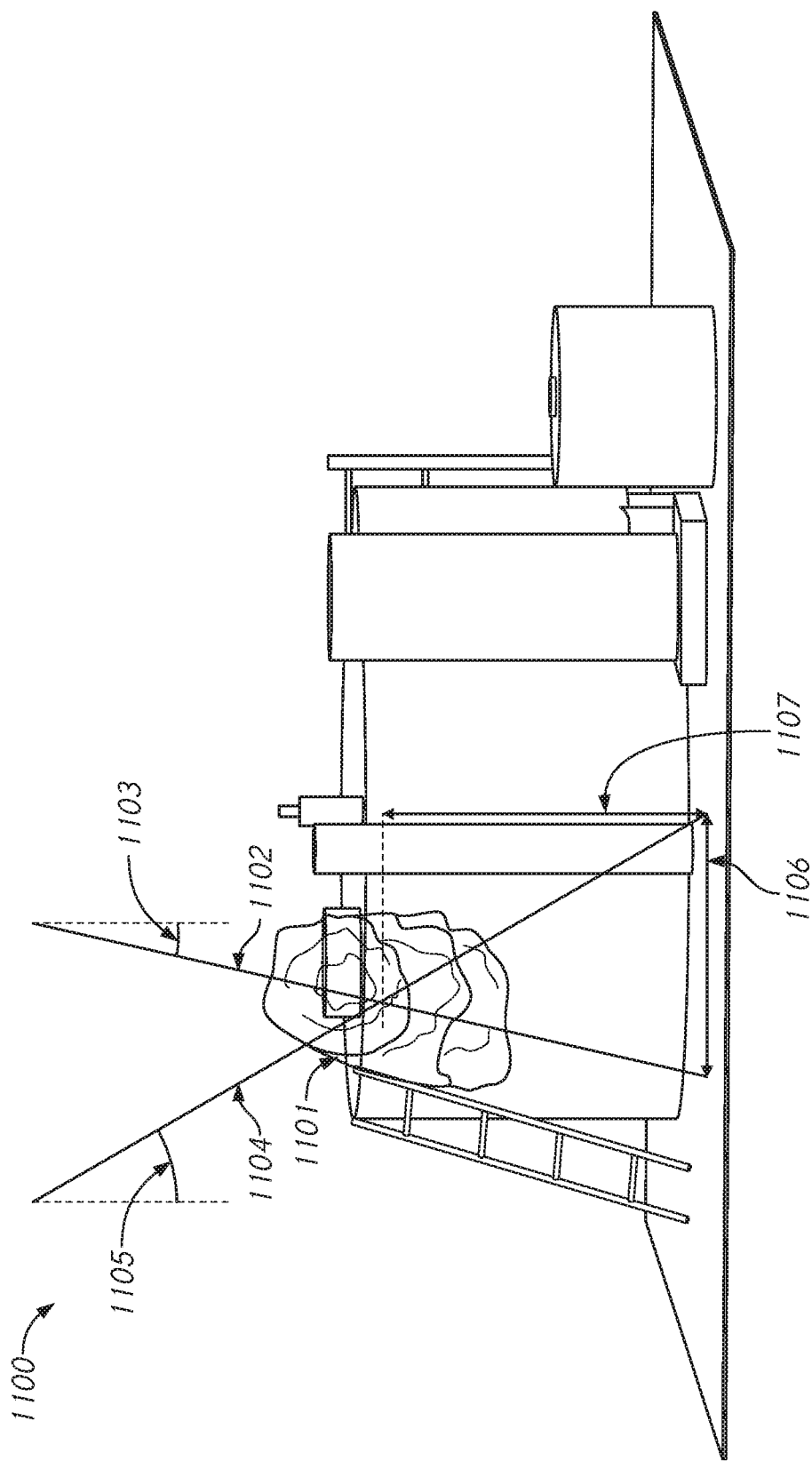
FIG. 11 is a block diagram of an environment with a gas plume according to an embodiment of the present disclosure.
Figure 12:
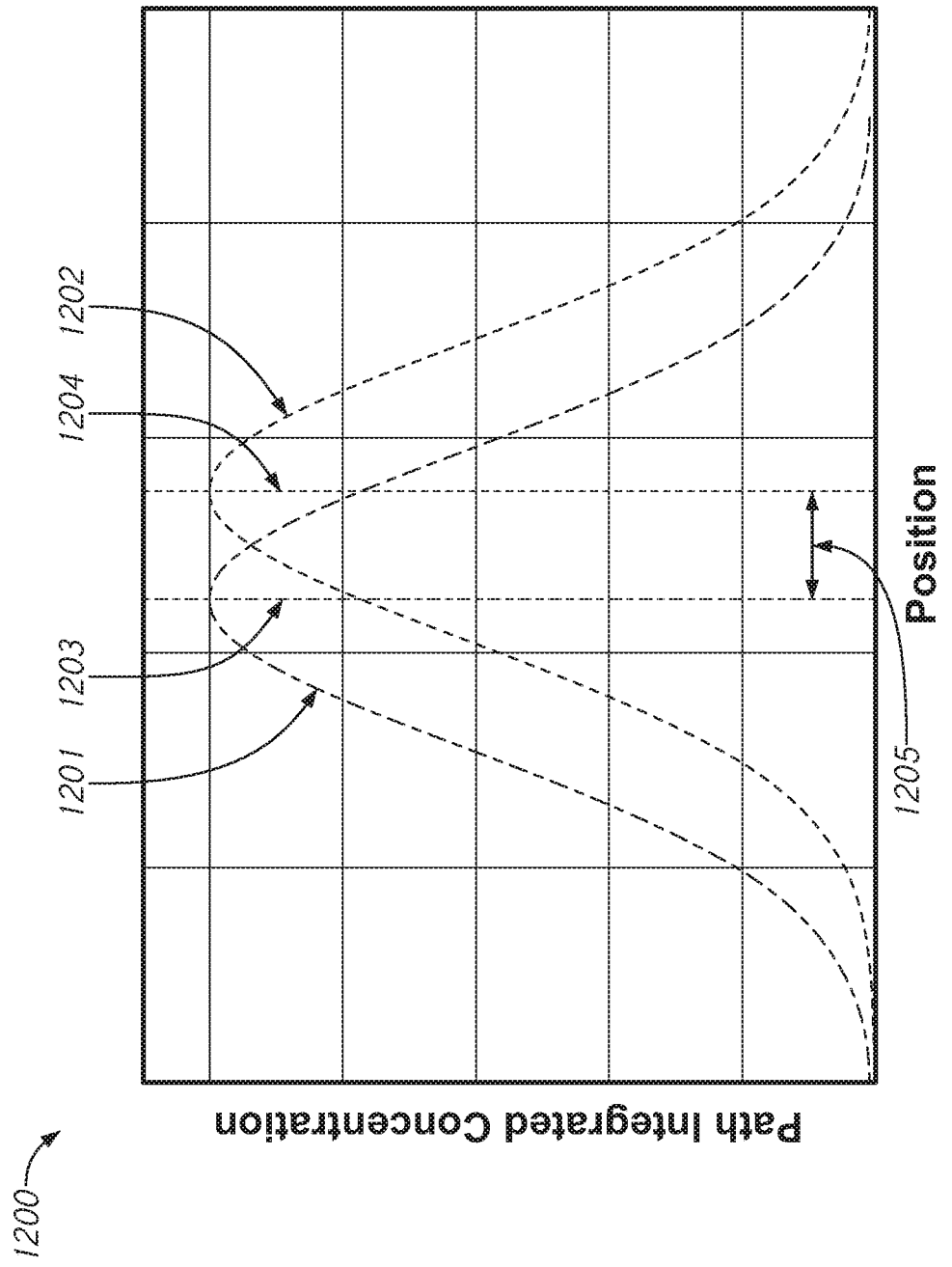
FIG. 12 is a graph depicting gas concentration cross sections according to an embodiment of the present disclosure
Figure 13:
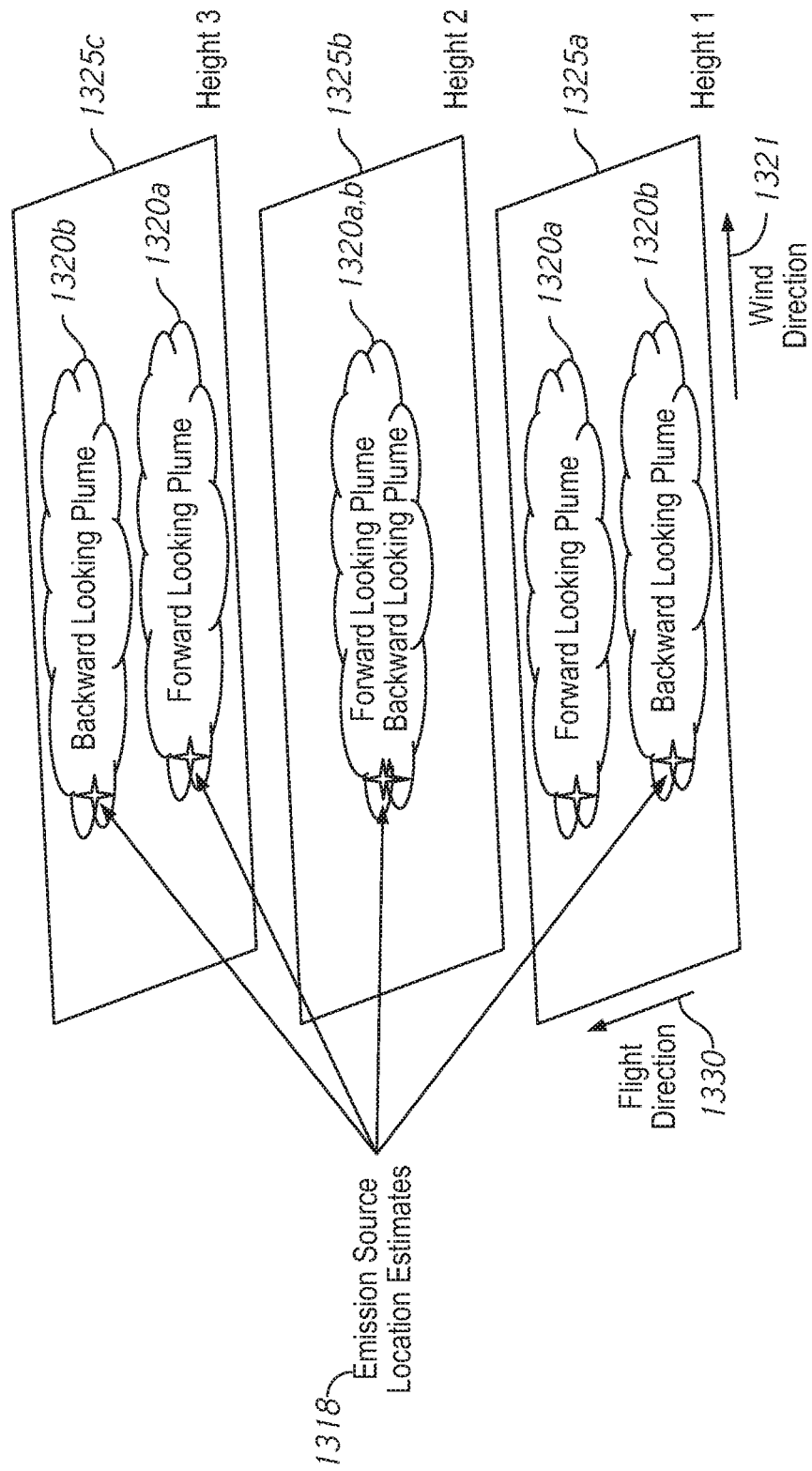
FIG. 13 is a block diagram of forward and backward facing measurement sets according to an embodiment of the present disclosure.

In some situations, a wind speed measurement may be taken at a first height, which may be different than the height of the gas plume. Wind speed may be strongly correlated to height above the ground, and so it may be important to determine a vertical wind speed profile and use a wind speed which matches a height of the gas concentration. For example, a wind model may be used to adjust the wind speed at the measurement height to match the wind speed at the gas plume height. FIG. 8 illustrates an example wind model which may be used to determine the wind speed at the gas plume height. FIG. 9 illustrates a first example method of measuring the height of the gas plume based on topography. FIGS. 10-12 illustrate a second example method of measuring the height of the gas plume based on triangulation. FIG. 13 illustrates a third example method of grouping measurements into forward and backward facing measurement groups. FIGS. 14-16 illustrate a method of determining a matrix of gas concentrations based on tomographic sectioning.

FIG. 8 is a graph of a vertical wind speed profile according to an embodiment of the present disclosure. The vertical wind speed profile may implement the wind model 228 of FIG. 2, in some embodiments. The x-axis of the graph 800 shows the height above the ground z, in meters. The y-axis of the graph 800 shows the wind speed at that height in m/s. While the graph 800 shows certain example scales along the x and y axes, other values may be used in other examples. The wind speed profile in the graph 800 may represent a particular method of determining a model of wind speed with height. The model may be used to relate wind measurements made at a first height to a wind speed at the height of the gas plume (e.g., which may be determined by any method including those described herein, for example, in FIGS. 9, 10-12, and/or 13-15).

The graph 800 shows anemometer measurements 801 at four heights above ground fitted with a logarithmic profile 802. The functional form of the logarithmic wind speed profile may be represented by equation 8, below:

$$\vec{u}(z) = u_0 \ln\left(\frac{z - z_d}{z_0} + \psi(z, z_0, L)\right)\hat{u} \qquad \text{Eqn. 8}$$

where u0 is the velocity coefficient, $\hat{u}$ is a unit vector in the direction of the wind, z is the height above ground, zd is the zero-plane displacement, z0 is the surface roughness parameter, $\psi$ is the atmospheric stability parameter and L is the Obukhov length. The values of the various coefficients may be determined based on measurements of the environment and/or may be estimated by, for example, looking up values matching similar conditions to the environment containing the gas plume. Based on the wind model expressed in FIG. 8, the wind speed at an arbitrary height may be calculated based on a measured wind speed at a known height. The height of the gas plume may be plugged into equation 8, which may return a value of the wind speed at that height. This may be used to develop a vertical profile of wind speeds.

FIG. 8 represents an example scenario with certain measurement and fitting conditions in order to illustrate how Equation 8 may be used. Other fitting parameters may be used in other scenarios. Neutral stability conditions were assumed for fitting the data shown in FIG. 8, such that $\psi=0$, and the resulting fit parameters 803 are shown in the inset. The velocity coefficient u0 was set to 0.39 m/s, the zero-plane displacement zd was set to 0.02 m, and the surface roughness parameter z0 was set to 0.003 m.

The example wind data shown in FIG. 8 represents measurements taken in an open field with short grass resulting in relatively small values for the zero-displacement plane ($z_d$) and surface roughness ($z_0$). For many gas leak quantification measurement scenarios wind speed versus height data may not available, and estimates for the values of $z_d$ and $z_0$ may be used to formulate a logarithmic wind profile. In this case values for $z_d$ and $z_0$ may be estimated using a basic rules, tables that specify the surface roughness for various terrain types and observations of measurement scene terrain type. In some embodiments, $z_d$ may generally be approximated as ⅔ of the average height of obstacles in the measurement scene. A rough approximation for $z_0$ may be computed as 1/20 the average height of obstacles in the measurement scene. A more refined value for $z_0$ may be derived using tables that list the accepted value of $z_0$ for a wide variety of terrain types. Furthermore, 3D data (e.g., generated by lidar or photogrammetry) of the measurement scene may be used to create a digital elevation model (which is a 3D computer graphics representation of a terrain's surface that may be created from a terrain's elevation data) of the ground surface in the region where the flux estimate is performed. Direct measurements of the variations in ground surface height, vegetation height and the height of structures in the measurement scene may result in further improvements to estimates of the $z_0$ parameter.

FIG. 9 is a block diagram showing a gas plume in an environment according to an embodiment of the present disclosure. The environment contains a gas plume 901 which is emitted from a source 902. It may be desirable to determine the height of the gas plume 901 above the terrain at a given location 905 in order to determine the wind speed at the location of the gas plume. FIG. 9 shows a method of using 3D topographic information to determine the height of the gas plume 901 at the location 905. The location 905 may represent a location of unperturbed wind flow.

The location of the source 902 may be determined. In some embodiments, the location of the source 902 may be determined based on gas plume images. In some embodiments, the location of the source 902 may be determined via other means and/or may be previously known. In some embodiments, the height 903 of the of the source 902 may be determined by subtracting a vertical coordinate of the emission location 902 in the topographic data from the average vertical coordinate of the neighboring ground surface. A digital elevation model of the ground surface using the topographic data may be used to determine the location of the neighboring ground and then determine its average vertical coordinate.

The gas plume 901 may change in height over distance as it is blown away from the source 902. This may be due, for example, to the buoyancy of the gas plume 901 compared to the ambient air, wind flow, and/or other features of the environment. The location 905 may be a horizontal distance 904 away from the source 902. In some embodiments, particularly where the distance 904 is small, the height of the source 903 may be used as the height of the gas plume 901 at the location 905. In some embodiments, a flow model (e.g., a buoyancy model) may be used to determine an expected different between the height at the source 903 and the height at the location 905 based on the distance 904.

The determined height of the gas plume 901 at the location 905 may be used (e.g., with Equation 8) to determine the wind speed at the location 905. Once the wind speed is known, optionally as a function of space, it may be used to determine the flux.

FIG. 10 is a block diagram of an example measurement pattern according to an embodiment of the present disclosure. FIG. 10 shows a measurement system 1000 which may be the measurement system 100 of FIG. 1 in some embodiments. The measurement system 1000 includes an optical system, which in the example of FIG. 10 may be a lidar sensor mounted to a mobile platform, which is an aircraft 1001 in this example. The measurement system of FIG. 10 may be used to generate the measurements which make up the gas plume image.

The measurement system 1000 may emit a lidar beam 1002, which may be used to collect gas concentration measurements. The lidar beam 1002 may have an elevation angle 1005 and azimuth angle 1004 with respect to the aircraft 1001. The lidar beam 1002 may be scanned by rotating the lidar beam 1002 about a vertical axis (e.g., by changing the azimuth angle 1004). In some embodiments the elevation angle 1005 may be kept constant, and the lidar beam 1002 may be scanned in an approximately circular pattern (disregarding motion of the aircraft 1001). Each of the measurements collected by the measurement system 1000 may be specified as by a beam direction 1002 that terminates at topographic surface location 1003, with the beam direction 1002 corresponding to azimuth angle 1004 and elevation angle 1005 relative to nadir. As the vehicle moves, the scan pattern may be 'pushed' over the measurement area resulting in measurement pattern 1006 that may be used to create gas concentration imagery. In some embodiments, the irregularly spaced points in scan pattern 1006 may be interpolated onto a grid pattern.

The measurement system 1000 may generate measurements of a given location 1003 from a plurality of different angles 1005. For example, in some embodiments, a given location 1003 may be measured by a forward looking direction of the lidar beam 1002 and a 'backward looking' direction of the lidar beam 1002. Measurements may be segregated into forward- and backward-looking sets to enable analysis, such as gas plume triangulation to determine the average plume height above ground (e.g., as discussed in FIGS. 11-13).

In some embodiments, it may be desirable to 'push' the scan pattern across the plume perpendicular to the wind direction (plume heading) to improve the accuracy of the height determination. In some embodiments, the measurement system 1000 may enable rapid acquisition of gas concentration images from two, or more, measurement angles such that minimal plume evolution occurs between the measurements, which may result in high-accuracy estimates of the average plume height.

FIG. 11 is a block diagram of an environment with a gas plume according to an embodiment of the present disclosure. FIG. 11 illustrates a method of determining the height of a gas plume vertical statistical moment using triangulation. In this figure, gas concentration measurement paths 1102 and 1104 pass through the center of gas plume 1101 at angles 1103 and 1105 relative to the vertical direction. The measurement paths 1102 and 1104 may be taken from the measurement system 1000 of FIG. 10 in some embodiments. In some embodiments, one measurement may be a forward-looking measurement, while the other may be a backward looking measurement as the aircraft 1001 moves past the gas source. Alternatively, the different angles may be obtained by different flight passes of the airborne platform, or by any other means.

The difference in the locations where the measurement paths 1102 and 1104 terminate on the backscattering target (e.g., the terrain) give rise to a horizontal displacement 1106 which may be used to compute the average plume height 1107 of the gas plume. The horizontal displacement 1106 may be determined based on the measured gas concentrations, as discussed in more detail in FIG. 12. Assuming a horizontal planar surface backscattering target, the horizontal displacement (d) may be combined with the measurement angles relative to the vertical direction θ1 and θ2 to compute the average plume height (h) according to Equation 9, below:

$$h = \frac{d}{\tan\theta_1 + \tan\theta_2} \qquad \text{Eqn. 9}$$

In cases where the topography of the backscattering surface is more complicated, 3D topography lidar data may be used to compensate for the surface complexity, and allow computation of the horizontal displacement for an arbitrary horizontal plane height. Equation 9 may then be used to compute the average plume height relative to the height of the horizontal plane where the displacement was computed. The plume height determined from equation 9 may then be used to determine a wind speed at that height (e.g., with Equation 8).

FIG. 12 is a graph depicting gas concentration cross sections according to an embodiment of the present disclosure. The graph 1200 shows idealized plume concentration cross sections 1201 and 1202 from gas concentration images taken at different measurements angles that may be used for estimating the height of the gas plume. The data in the graph 1200 may represent data acquired by the measurement system 1000 of FIG. 10 (and/or 100 of FIG. 1) and may be used to calculate a displacement between the measurements, which in turn, may be used to calculate a height of the gas plume as discussed in regard to Equation 9.

The gas plume cross sections 1201 and 1202 are separated by a displacement 1205 based on the different angles from which each of the cross sections 1201 and 1202 were taken. Since the gas plume cross sections 1201 and 1202 are perpendicular to the plume direction (which may be associated with the wind direction), the peak concentration may generally be expected to be associated with a middle of the gas plume. Gas plume cross sections that are perpendicular to the plume heading may be obtained from gas concentration image data by interpolating along lines perpendicular to the estimated plume heading direction. A method for determining the plume heading based on gas concentration images is discussed in FIGS. 4-5.

The average positions of the plume cross sections 1203 and 1204, projected onto the hard target background, may be determined using several methods including fitting procedures or center of mass computations, and the position difference may be computed to determine the horizontal displacement 1205. Alternately, signal processing techniques, such as a cross-correlation, may be performed to determine the horizontal displacement 1205. Once the displacement is known, it may be used in Equation 9 (along with the measurement angles, which may generally be known from the geometry of the measurement system) to determine a height of the gas plume. This, in turn, may be used to help determine a wind speed at the location of the gas plume.

FIG. 13 is a block diagram of forward and backward facing measurement sets according to an embodiment of the present disclosure. FIG. 13 represents another example method of determining plume height (e.g., a gas concentration statistical moment), and may implement step 220 of FIG. 2 in some embodiments. In the example embodiment of FIG. 13, gas concentration measurements are segregated into a first angle group 1320a and second angle group 1320b of measurements. An angle group may comprise multiple gas concentration measurements from one or a set of measurement angles relative to a gas plume. The first angle group 1320a and second angle group 1320b measurements may be, for example, forward-looking and backward-looking measurements (relative to the aircraft motion direction), and may be segregated by computing the dot product of the LiDAR beam vector with the aircraft velocity vector. In this example, LiDAR measurements with velocity vector dot products greater than zero may be considered forward-looking, while LiDAR measurements with velocity vector dot product less than zero may be considered backward looking. The sensor position, LiDAR beam vector, path-integrated gas concentration and range to target for each measurement may be used to create plume images for the forward- and backward-looking measurement sets. The forward- and backward-looking plume images may then be projected onto horizontal planes 1325a-c of varying heights by appropriately modifying the target range for each measurement. The spatial overlap between forward- and backward-looking plume images 1320a-b may be computed at multiple horizontal plane heights 1325a-c. The horizontal plane height that corresponds to the best plume overlap (e.g., in this case height 1325b) between the forward- and backward-looking measurement sets 1320a-b may indicate a good estimate of the actual plume height.

One method of computing and/or quantifying the plume overlap may involve interpolation of the forward- and backward-looking plume images 1320a-b onto a common spatial grid and using a mean squared error computation as a metric for plume overlap. Prior to the plume overlap computation, it may be useful to filter the forward- and backward-looking plume images 1320a-b by setting the concentration value of pixels below specified gas concentration threshold to zero to improve the discrimination of the plume overlap metric. As illustrated in FIG. 13, the plume height may correspond to the horizontal plane with the lowest mean squared error between the forward- and backward-looking plumes. The plume height may be determined relative to topographic targets within the area covered by the plume images using the 3D LiDAR data. In some cases, the plume height may change with distance from the emission source. The plume overlap approach disclosed herein may be used to determine the plume height as a function of distance from the emission source by performing plume overlap analysis on sections of the plume at different distances from the emission source.

In addition to identifying a specific plume height, related analysis and methods may also be useful for identifying, and optionally disregarding, weighting, filtering, or otherwise treating differently, plumes that may not be near the ground (or a ground structure) and/or may not originate from within the field of regard of the sensor. For instance, a plume originating from leak 1318 that is outside the field of regard of the sensor may drift into the field of regard of the sensor and may be at a greater height than plumes originating from within the field of regard of the sensor. It may be desirable to separate or disregard such a plume so as not to confuse the plume with plumes originating from within the sensor field of regard. It may be possible to develop a processing algorithm to ignore, disregard, weight, filter, or otherwise treat differently plumes for which the first-angle group (e.g. forward-looking) and the second-angle group (e.g. backward-looking) measurements lack overlap, as measured by one or more metrics. A metric may be the separation between the plume centers of mass (which correspond to the first and second angle groups), the ratio of the separation between the plume centers of mass divided by the plume variance, or any other metric by which the first-angle group and the second-angle group measurements are compared. The space over which the overlap of the first-angle group and the second-angle group is assessed may be spatial, angular, or other. Plume measurements with an overlap between the first-angle group and the second-angle group that is less than the metric threshold may be disregarded, weighted, filtered, or otherwise treated differently than plume measurements with an overlap that is greater than the metric threshold. Any such filtering may be one of multiple filtering steps, any of which may be used alone or in combination with other filtering steps.

Another filtering step may include determining if there is a physical structure in proximity to a high plume. For instance, an emission stack may be high off the ground and therefore may emit a plume that is high relative to the ground. The plume from such a structure may therefore exhibit poor spatial overlap between the first angle group and the second angle group. However, it may not be desirable to disregard, weight, filter, or otherwise treat the plume differently from plumes that are close to the ground. Therefore, the proximity of a plume to a physical structure or possible emission point may be used for decision-making or filtering regarding whether to disregard, weight, filter, or otherwise treat differently the plume. The presence of the structure vertical extent may be determined by topographical data (e.g. LiDAR, photogrammetry), or by any other means.

Similarly, another filtering step may include defining a metric corresponding to a plume spatial or angular variance because greater plume spread or variance may be associated with greater plume height or distance from an emission source. In this case, a plume that is high above the ground may have poor spatial overlap between the first angle group and the second angle group (e.g. the separation of the centers of masses between the plumes may be large or above a threshold), which may indicate that the plume is high above the ground. However, the plume spatial or angular variance may be small (e.g. below a threshold), indicating that the plume is near an emission source. Again, such a metric may be used for decision-making regarding whether to disregard, weight, filter, or otherwise treat differently the plume.

More generally, tomographic reconstruction, which may use gas measurements from multiple angles, may be used to determine vertical gas distribution to enable more accurate gas flux determination. An example measurement scheme for acquiring LiDAR measurements that may be suitable for tomographic reconstruction to determine vertical gas concentration distributions is shown in FIGS. 14-16. Any of the steps depicted in FIGS. 14-16 may be implemented by the measurement system 100 of FIG. 1 and/or performed by the computing system 200 of FIG. 2.

FIG. 14 is a block diagram of a measurement system according to an embodiment of the present disclosure. The measurement system 1400 may be an implementation of the measurement system 100 of FIG. 1, and may generally be similar to the measurement system 1000 of FIG. 10. The measurement system 1400 includes a LiDAR sensor mounted on an aircraft 1401. The measurement system 1400 is outfitted with a beam scanner that enables acquisition of integrated-path gas concentration measurements and target range measurements at more than one angle with respect to the nadir direction, as shown by the plurality of lidar beam paths 1402. A portion of the laser light transmitted from the LiDAR sensor along the beam paths 1402 is reflected from the backscatter target 1403 (e.g., the terrain) and received by the LiDAR sensor in the aircraft 1401. The received backscatter laser light may then be processed to determine the range to the backscatter target and the path-integrated gas concentration between the sensor and the backscatter target.

FIG. 15 is a block diagram of a measurement system according to an embodiment of the present disclosure. The measurement system 1500 may be the same as the measurement system 1400 of FIG. 14 in some embodiments. FIG. 15 shows an example method of segmenting data that may be used to aid tomographic reconstruction of gas plume data. As the aircraft 1502 moves through the air, LiDAR measurements may be periodically acquired from multiple directions relative to nadir (e.g., along the beam paths 1502) to form a set of measurements that may be used for tomographic reconstruction. In the example of FIG. 154, the region between the aircraft and backscatter targets is divided into set of grid cells, with each cell having a unique index (j). Each individual LiDAR measurement within the set of LiDAR measurements that traverse the grid cells (j) is labeled with a unique index (i). Tomographic inversion of the path-integrated gas concentration measurements such that a gas concentration is determined for each grid cell may be performed based on, for instance, Equation 10, below:

$$b_i = \Sigma_j^N A_{ij} x_j \qquad \text{Eqn. 10}$$

Here, bi is the path-integrated gas concentration measurement along the ith measurement direction, Aij is the chord length along the ith direction inside the jth grid cell and xj is the gas concentration in the jth grid cell. Knowledge of surface topography and/or range measurements (which may be co-aligned with the LIDAR measurements) may be useful to establish the grid and/or to determine the chord length within a given grid cell.

In some cases it may be difficult to acquire sufficient concentration measurements (bi) to invert equation 10 directly. Based on the aircraft and sensor parameters acquiring sufficient spatial resolution for direct inversion of equation 10 may be impractical, or the additional acquisition time may allow the plume position to evolve during the measurement duration, both of which may hinder tomographic reconstruction. This problem can be mitigated by rapidly acquiring coarse spatial resolution measurements and applying one of a number of techniques for spanning the null space of an under-sampled reconstruction grid. Examples include Tikihonov regularization, Landweber iteration, interpolation of the concentration measurements (bi) and/or functional fitting of the plumes measured from each position.

It may be particularly important to determine the gas concentration as a function of vertical position (height) since the wind speed may be known to also depend on height. Vertical gas concentration profiles (Cz) may be constructed, such as the column 1504 shown in FIG. 15, based on assembling vertically aligned gas concentration grid cells (j). If the vertical wind profile for this location is also known, or can be estimated, the flux ($\Phi_x$) corresponding to this column may be computed using Equation 11, below:

$$\Phi_x = \Sigma_z^{N_z} C_z \hat{n} \cdot \vec{u} z \Delta z \qquad \text{Eqn. 11}$$

Here $\vec{u}_z$ is the wind velocity at the of the zth cell along the vertical column, n̂ is the unit vector in the direction normal to the column and $\Delta z$ is the grid cell size in the vertical dimension. In this way, the gas flux for a vertical column may be effectively determined by vertically integrating the vertically varying plume concentration, multiplied by the vertically varying wind speed as shown in equation 11. This method can produce significant improvements in gas flux estimates due to the typically significant vertical wind speed variations.

FIG. 16 is a block diagram of a measurement system according to an embodiment of the present disclosure. The measurement system 1600 may be an implementation of the measurement system 100 of FIG. 1, and may be generally similar to the measurement systems 1400 of FIG. 14 and/or 1500 of FIG. 15. FIG. 16 shows an example method of determining the total flux from a gas source (e.g., a gas leak) based on the flux from individual columns, which may be determined as discussed in FIG. 15.

Once the flux for individual columns ($\Phi_x$) has been estimated (e.g., using Equation 11) the total flux for an emission source may be determined. The LiDAR sensor mounted in aircraft 1602 acquires a set of LiDAR measurements, (similar to the measurements 1502 of FIG. 15), that is inputted into a tomographic inversion algorithm to determine the gas concentration in each cell of grid 1603. The grid cell gas concentration data may then be used to create vertical gas concentration profiles, such as 1604, for different locations along the aircraft flight path. A plane for tomographic inversion of gas concentrations, and hence flux estimation, 1605 may be selected using the gas concentration imagery, wind direction information and locations of objects obstructing the wind field to identify a location within a gas plume 1606 that may be suitable for flux estimation. For example, a region of unperturbed wind flow may be chosen. Flux measurements ($\Phi_x$) for individual columns may then be summed across the plume 1606 to determine the total flux for the emission source ($\Phi_e$) 1601 using Equation 12, below:

$$\Phi_e = \Sigma_x^{N_x} \Phi_x \Delta x \qquad \text{Eqn. 12}$$

Here, $\Delta x$ is the grid cell size in the horizontal direction and $N_x$ is the number of vertical columns being integrated. The vertical column flux measurements summed to determine the total flux from an emission source may comprise one or many planes and may or may not enclose the emission source location.

For brevity, the operation of the optical systems herein have generally been described with respect to light being emitted by the optical system towards a target area. However, one of skill in the art would appreciate that since optical paths may typically be reversible, the beam path may also represent a field of view 'seen' by the optical system (e.g., reach a receiver of the optical system).

Certain materials have been described herein based on their interaction with light (e.g., opaque, reflective, transmissive, etc.). These descriptors may refer to that material's interactions with a range of wavelength(s) emitted by the system and/or that the receiver is sensitive to. It would be understood by one of skill in the art that a given material's properties vary at different ranges of wavelengths and that different materials may be desired for different expected ranges of wavelength(s). The description of a particular example material is not intended to limit the disclosure to a range of wavelengths over which that particular example material has the desired optical properties. The term 'light' may be used throughout the spectrum to represent electromagnetic radiation, and is not intended to limit the disclosure to electromagnetic radiation within the visible spectrum. The term 'light' may refer to electromagnetic radiation of any wavelength.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
   collecting a gas plume image comprising a plurality of gas concentration measurements of a gas plume in an environment;
   determining a direction of the gas plume based on the gas plume image;
   determining one or more gas concentration integrals by integrating selected ones of the plurality of gas concentration measurements along a line which is generally perpendicular to the direction of the gas plume;
   determining a gas concentration profile based on a gas concentration metric as a property of distance along the direction of the gas plume, wherein the gas concentration metric is based on the plurality of gas concentration measurements, wherein determining the gas concentration profile includes generating the gas concentration profile by plotting the gas concentration integrals as the gas concentration metric;
   selecting a spatial region of unperturbed flow of the gas plume where the gas plume has a uniform flow based on a range of distances along the gas concentration profile where the gas concentration metric has a low variation, wherein the region of unperturbed flow is a portion of the environment;
   determining a wind speed associated with the region of unperturbed flow; and
   determining a gas flux based on at least one of the gas concentration measurements located in the region of unperturbed flow and the wind speed.

2. The method of claim 1, further comprising:
   determining a vertical statistical moment or vertical distribution of the gas plume associated with the region of unperturbed flow;
   determining a vertical wind speed profile associated with the region of unperturbed flow; and
   determining the gas flux based on the vertical statistical moment or vertical distribution and the vertical wind speed profile.

3. The method of claim 1, wherein determining the region of unperturbed flow is additionally based on a topographic map of the environment.

4. The method of claim 3, further comprising:
scanning a beam across a target area in the environment to collect the plurality of gas concentration measurements;
determining a plurality of range measurements of a distance along the beam to a surface in the target area while collecting the plurality of gas concentration measurements; and
generating the topographic map based on the plurality of range measurements.

5. The method of claim 1, further comprising, based on the determined gas flux, evacuating an area, measuring an environmental hazard, locating a gas leak, determining a possible repair, conducting a repair, ensuring regulatory compliance, or combinations thereof.

6. The method of claim 1, further comprising:
filtering the plurality of gas concentration measurements to select ones of the gas concentration measurements which are within the region of unperturbed flow; and
determining the gas flux based on the selected ones of the plurality of gas concentration measurements.

7. The method of claim 1, wherein the region of unperturbed flow is unobstructed by physical obstructions, dynamics from a pressurized leak, or combinations thereof.

8. The method of claim 1, further comprising:
determining a heading of the wind velocity; and
determining the region of unperturbed flow based, in part on the heading.

9. The method of claim 1, further comprising:
determining a boundary of the region of unperturbed flow; and
determining a wind velocity at a location inside the boundary.

10. The method of claim 1, wherein in the region of unperturbed flow the flow of the gas plume is unperturbed by obstructions.

11. The method of claim 1, wherein the spatial region where the gas concentration metric has a low variation is determined by a low derivative with respect to distance along the gas concentration profile.

12. The method of claim 1, further comprising:
determining the range of distances before a diffusion region of the gas concentration profile.

* * * * *